United States Patent
Goodwin et al.

(10) Patent No.: US 7,194,902 B1
(45) Date of Patent: Mar. 27, 2007

(54) APPARATUS AND METHOD FOR FORMATION EVALUATION

(75) Inventors: Anthony R. H. Goodwin, Sugar Land, TX (US); Kai Hsu, Sugar Land, TX (US); Michael W. Frels, Richmond, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/022,142

(22) Filed: Dec. 23, 2004

Related U.S. Application Data

(63) Continuation-in-part of application No. 11/021,849, filed on Dec. 23, 2004.

(51) Int. Cl.
*G01N 11/00* (2006.01)
(52) U.S. Cl. .................. 73/152.24; 73/54.02
(58) Field of Classification Search ............ 73/152.24
See application file for complete search history.

(56) References Cited

U.S. PATENT DOCUMENTS

| | | | |
|---|---|---|---|
| 3,130,808 A | 4/1964 | Walker, Jr. et al. | |
| 3,346,058 A | 10/1967 | Bouyoucos | |
| 3,390,737 A | 7/1968 | Johnson | |
| 3,449,940 A | 6/1969 | Banks | |
| 3,608,715 A | 9/1971 | Snyder et al. | |
| 3,903,732 A | 9/1975 | Rork et al. | |
| 4,291,583 A * | 9/1981 | Buike | 73/861.75 |
| 4,319,191 A | 3/1982 | Meador et al. | |
| 4,526,480 A | 7/1985 | Ward | |
| 4,574,639 A | 3/1986 | Ward | |
| 4,602,505 A | 7/1986 | Kanda et al. | |
| 4,651,101 A | 3/1987 | Barber et al. | |
| 4,655,075 A * | 4/1987 | Albert et al. | 73/32 A |

(Continued)

FOREIGN PATENT DOCUMENTS

EP 0282251 3/1988

(Continued)

OTHER PUBLICATIONS

Field Trials of the Viscosity & Fluid Density Tool (VFD) News Release; Nan Gall Technology Limited, published Aug. 2002, 1 pp.

(Continued)

*Primary Examiner*—Robert Raevis
(74) *Attorney, Agent, or Firm*—Matthias Abrell; Kevin P. McEnane; William Batzer

(57) ABSTRACT

A viscometer-densimeter for a down hole tool positionable in a well bore penetrating a subterranean formation is described. The formation contains at least one fluid therein. The down hole tool is adapted to convey at least a portion of the fluid to the viscometer-densimeter. The viscometer-densimeter comprises a sensor unit, and at least one magnet. The sensor unit is positionable within the down hole tool and comprises at least two spatially disposed connectors and a wire suspended in tension between the at least two connectors such that the wire is available for interaction with the fluid when the viscometer-densimeter is positioned within the down hole tool and the down hole tool is positioned within the subterranean formation and receives the fluid from the subterranean formation. The connectors and the wire are constructed so as to provide a frequency oscillator.

10 Claims, 13 Drawing Sheets

U.S. PATENT DOCUMENTS

| | | | |
|---|---|---|---|
| 4,679,427 | A | 7/1987 | Kanda et al. |
| 4,729,237 | A | 3/1988 | Suzuki et al. |
| 4,922,745 | A | 5/1990 | Rudkin et al. |
| 5,006,845 | A | 4/1991 | Calcar et al. |
| 5,048,351 | A | 9/1991 | Dames |
| 5,115,198 | A | 5/1992 | Gianzero et al. |
| 5,204,529 | A | 4/1993 | Diatschenko |
| 5,269,188 | A | 12/1993 | Esin et al. |
| 5,361,632 | A | 11/1994 | Magnani |
| 5,565,620 | A * | 10/1996 | Bohlin .................... 73/54.25 |
| 5,622,223 | A | 4/1997 | Vasquez |
| 5,734,098 | A | 3/1998 | Kraus et al. |
| 5,741,962 | A | 4/1998 | Brichak et al. |
| 5,757,191 | A | 5/1998 | Gianzero et al. |
| 5,837,893 | A | 11/1998 | Chu |
| 6,073,492 | A | 6/2000 | Rosselson et al. |
| 6,138,949 | A | 10/2000 | Manende et al. |
| 6,147,496 | A | 11/2000 | Strack et al. |
| 6,163,155 | A | 12/2000 | Bittar |
| 6,176,323 | B1 | 1/2001 | Weirich et al. |
| 6,182,499 | B1 | 2/2001 | McFarland et al. |
| 6,336,353 | B2 | 1/2002 | Matsiev et al. |
| 6,357,536 | B1 | 3/2002 | Schrader et al. |
| 6,378,364 | B1 | 4/2002 | Pelletier et al. |
| 6,393,895 | B1 | 5/2002 | Matsiev et al. |
| 6,401,519 | B1 | 6/2002 | McFarland et al. |
| 6,494,079 | B1 | 12/2002 | Matsiev et al. |
| 6,543,281 | B2 | 4/2003 | Pelletier et al. |
| 2002/0194906 | A1 | 12/2002 | Goodwin et al. |
| 2004/0139798 | A1 | 7/2004 | Haddad et al. |

FOREIGN PATENT DOCUMENTS

| | | |
|---|---|---|
| EP | 1306659 | 5/2003 |
| GB | 1266939 | 3/1972 |
| GB | 2392980 | 3/2004 |
| WO | WO01/51898 | 7/2001 |
| WO | WO02/099414 | 12/2002 |

OTHER PUBLICATIONS

<http://www.nangall/com/products/plt/Fluid_Density_Tuned.htm;> Fluid Density (Tuned) VFD Tool; printed Dec. 10, 2004; Nan Gall Energy; pp. 1-2.

Van der Gulik et al., Vibrating-Wire Viscometer, Chapter 4 in Experimental Thermodynamics, vol. 3, 1991, Blackwell Scientific Publications, pp. 79-88.

"PVT Express; Delivering Early Fluid Analysis Data;" Schlumberger pamphlet; Jun. 2003; pp. 1-5.

"Advanced Fluid Characterization; Hydrocarbon Identification and Analysis Using NMR;" Schlumberger pamphlet; Sep. 2002; pp. 1-8.

<http://www.exprogroup.com/corpus/VTFFD/vtffd.asp?Level1_ID=1;> "Vibrating Tuning Fork Fluid Density Tool;" The Expro Group; printed Nov. 23, 2004; 1 pp.

Caudwell et al., "A Robust Vibrating Wire Viscometer for Reservoir Fluids: results for toluene and $n$-decane;" Journal of Petroleum Science & Engineering 44 (2004); Feb. 2004; pp. 333-340.

Nikl, M., "Wide Band Gap Scintillation Materials: Progress in the Technology and Material Understanding;" Phys. Stat. Sol. 178; Jan. 2000; pp. 595-620.

Stokes, George Gabriel, "Mathematical and Physical Papers vol. 3;" Cambridge University Press 1901; pp. 1-65.

Retsina, T. et al., "The Theory of a Vibrating-Rod Viscometer;" Applied Scientific Research 43; 1987; pp. 325-346.

Retsina, T. et al., "The Theory of a Vibrating-Rod Densimeter;" Applied Scientific Research 43: 1986; pp. 127-158.

Avelino, H.M.T. et al., "Simultaneous Measurement of the Density and Viscosity of Compressed Liquid Toluene;" International Journal of Thermophysics, vol. 24, No. 2, Mar. 2003; pp. 323-336.

Tough, J.T. et al., "Viscosity of Liquid He II;" Physical Review vol. 132, No. 6, Dec. 1963; pp. 2373-2379.

Tough, J.t. et al., "Vibrating Wire Viscometer;" The Review of Scientific Instruments vol. 35, No. 10, Oct. 1964; pp. 1345-1348.

Goodwin, James et al., "A Vibrating Wire Viscometer for Measurements at Elevated Pressures;" Journal of Physics E: Scientific Instruments 1973 vol. 6; pp. 452-456, Jan. 1973.

Goodwin, J.M. et al., "The Viscosity of Pressurized He Above Tλ;" Physica 76 (1974) pp. 177-180, Mar. 1974.

Caetano, F. et al., "The Viscosity of Di-Isodecylphthalate;" to be published in International Journal of Tyermophysics; pp. 1-11, no date.

Caetano, F. et al., "Validation of a Vibrating Wire Viscometer: Measurements in the Range 0.5 to 135 mPa•s;" submitted to Journal of Chemical Engineering Data; pp. 1-20, no date.

Caudwell, Derek, "Viscosity of Dense Fluid Mixtures;" Department of Chemical Engineering and Chemical Technology, Imperial College London; Jun. 2004; pp. 1-195.

Bevington, P.R. et al., "Data Reduction and Error Analysis for the Physical Sciences," McGraw Hill, 1992, pp. 161-164.

\* cited by examiner

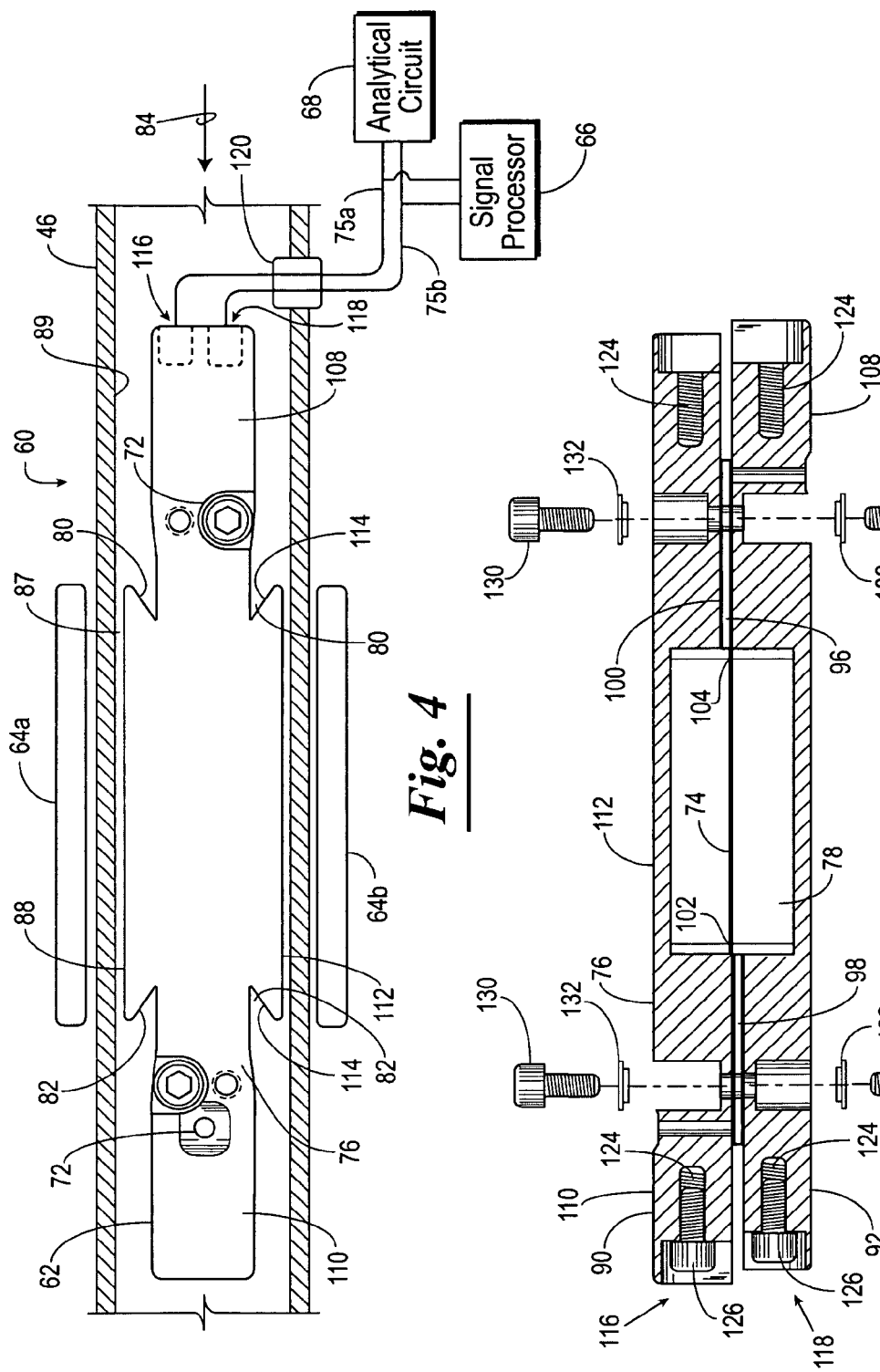

APPARATUS AND METHOD FOR FORMATION EVALUATION

CROSS REFERENCE TO RELATED APPLICATIONS

This application is a continuation in part of co-pending U.S. patent application Ser. No. 11/021,849 filed on Dec. 23, 2004.

BACKGROUND OF THE INVENTION

1. Field of the Invention

The present invention relates to techniques for performing formation evaluation of a subterranean formation by a down hole tool positioned in a well bore penetrating the subterranean formation. More particularly, but not by way of limitation, the present invention relates to techniques for determining fluid parameters, such as the viscosity and density of formation fluid drawn into and/or evaluated by the down hole tool.

2. Background of the Related Art

Well bores are drilled to locate and produce hydrocarbons. A down hole drilling tool with a bit at an end thereof is advanced into the ground to form a well bore. As the drilling tool is advanced, drilling mud is pumped through the drilling tool and out the drill bit to cool the drilling tool and carry away cuttings. The drilling mud additionally forms a mud cake that lines the well bore.

During the drilling operation, it is desirable to perform various evaluations of the formations penetrated by the well bore. In some cases, the drilling tool may be removed and a wire line tool may be deployed into the well bore to test and/or sample the formation. In other cases, the drilling tool may be provided with devices to test and/or sample the surrounding formation and the drilling tool may be used to perform the testing or sampling. These samples or tests may be used, for example, to locate valuable hydrocarbons.

Formation evaluation often requires that fluid from the formation be drawn into the down hole tool for testing and/or sampling. Various devices, such as probes, are extended from the down hole tool to establish fluid communication with the formation surrounding the well bore and to draw fluid into the down hole tool. A typical probe is a circular element extended from the down hole tool and positioned against the sidewall of the well bore. A rubber packer at the end of the probe is used to create a seal with the wall of the well bore. Another device used to form a seal with the well bore is referred to as a dual packer. With a dual packer, two elastomeric rings expand radially about the tool to isolate a portion of the well bore there between. The rings form a seal with the well bore wall and permit fluid to be drawn into the isolated portion of the well bore and into an inlet in the down hole tool.

The mud cake lining the well bore is often useful in assisting the probe and/or dual packers in making the seal with the well bore wall. Once the seal is made, fluid from the formation is drawn into the down hole tool through an inlet by lowering the pressure in the down hole tool. Examples of probes and/or packers used in down hole tools are described in U.S. Pat. Nos. 6,301,959; 4,860,581; 4,936,139; 6,585,045; 6,609,568 and 6,719,049 and U.S. Patent Application No. 2004/0000433.

Formation evaluation is typically performed on fluids drawn into the down hole tool. Techniques currently exist for performing various measurements, pretests and/or sample collection of fluids that enter the down hole tool. However, it has been discovered that when the formation fluid passes into the down hole tool, various contaminants, such as well bore fluids and/or drilling mud, may enter the tool with the formation fluids. These contaminates may affect the quality of measurements and/or samples of the formation fluids. Moreover, contamination may cause costly delays in the well bore operations by requiring additional time for more testing and/or sampling. Additionally, such problems may yield false results that are erroneous and/or unusable.

It is, therefore, desirable that the formation fluid entering into the down hole tool be sufficiently "clean" or "virgin" for valid testing. In other words, the formation fluid should have little or no contamination. Attempts have been made to eliminate contaminates from entering the down hole tool with the formation fluid. For example, as depicted in U.S. Pat. No. 4,951,749, filters have been positioned in probes to block contaminates from entering the down hole tool with the formation fluid. Additionally, as shown in U.S. Pat. No. 6,301,959 issued to Hrametz, a probe is provided with a guard ring to divert contaminated fluids away from clean fluid as it enters the probe. Fluid entering the down hole tool typically passes through flow lines and may be captured in a sample chamber or dumped into the well bore. Various valves, gauges and other components may be incorporated along the flow lines to divert, test and/or capture the fluid as it passes through the down hole tool.

Fluid passing through the down hole tool may be tested to determine various down hole parameters or properties. The thermophysical properties of hydrocarbon reservoir fluids, such as viscosity, density and phase behavior of the fluid at reservoir conditions, may be used to evaluate potential reserves, determine flow in porous media and design completion, separation, treating, and metering systems, among others.

Various techniques have been developed for determining viscosity of fluids. For example, viscometers having a bob suspended between fixation points for a torsion wire have also been proposed as described, for example, in U.S. Pat. Nos. 5,763,766 and 6,070,457. Viscometers have also been formed from vibrating objects. One such viscometer has been used in down hole applications for measuring the viscosity, density and dielectric constant of formation fluid or filtrate in a hydrocarbon producing well. For example, International Publication Number WO 02/093126 discloses a tuning fork resonator within a pipe to provide real-time direct measurements and estimates of the viscosity, density and dielectric constant of formation fluid or filtrate within the hydrocarbon producing well. Another viscometer, having a wire clamped between two posts has been used in a laboratory environment as described, for example in *The Viscosity of Pressurized He above $T_\lambda$*, Physica 76 (1974) 177–180; *Vibrating Wire Viscometer*, The Review of Scientific Instruments Vol. 35, No. 10 (October 1964) pgs. 1345–1348.

Despite the existence of techniques for measuring viscosity, there remains a need to provide accurate viscosity measurements down hole, and preferably without regard to the position of a sensor down hole relative to the gravitational field. It is desirable that such a system be capable of providing checks for precision and/or accuracy. It is further desirable that such a system be provided with a simple configuration adapted for use in a harsh well bore environment.

SUMMARY OF THE INVENTION

In one aspect, the present invention relates to a viscometer-densimeter for a down hole tool positionable in a well bore penetrating a subterranean formation. The down hole tool is adapted to convey at least a portion of a fluid in the formation to the viscometer-densimeter. The viscometer-densimeter includes a sensor unit positionable within the down hole tool. The sensor unit includes at least two spatially disposed connectors, a wire, and at least one magnet. The wire is suspended in tension between the at least two connectors such that the wire is available for interaction with the fluid when the viscometer-densimeter is positioned within the down hole tool and the down hole tool is positioned within the subterranean formation and receives the fluid from the subterranean formation. The connectors and the wire are constructed so as to provide a frequency oscillator. The at least one magnet emits a magnetic field interacting with the wire.

The connectors and the wire can be constructed of materials having similar coefficients of thermal expansion so as to provide the frequency oscillator. For example, the connectors and the wire can be constructed of a single type of material to substantially eliminate variations in the resonant frequency of the wire due to thermal and elastic deformation caused by down hole conditions. The viscometer-densimeter can also be provided with a flow tube in which the wire is suspended by the connectors, and in this instance the flow tube, the connectors and the wire are desirably constructed of materials having similar coefficients of thermal expansion so as to provide the frequency oscillator.

In another aspect, the sensor unit is further provided with a means for preventing rotation of the wire with respect to the connectors. The means for preventing rotation of the wire can include a boss connected to the wire with the boss having a non-circular cross-section.

In yet another aspect, the viscometer-densimeter is further provided with an analytical circuit receiving feedback from the wire for calculating at least two parameters (e.g., viscosity and density) of fluid interacting with the wire.

In yet another aspect, the present invention relates to a down hole tool positionable in a well bore having a wall and penetrating a subterranean formation. The formation typically has a fluid, such as natural gas or oil therein. The down hole tool is provided with a housing, a fluid communication device, and a viscometer-densimeter. The housing encloses at least one evaluation cavity. The fluid communication device is extendable from the housing for sealing engagement with the wall of the well bore. The fluid communication device has at least one inlet communicating with the evaluation cavity for receiving the fluid from the formation and depositing such fluid into the evaluation cavity. The viscometer-densimeter is provided with a sensor unit positioned within the evaluation cavity. The sensor unit is provided with at least two spatially disposed connectors, a wire and a magnet. The wire is suspended in tension between the at least two connectors such that the wire is available for interaction with the fluid within the evaluation cavity. The connectors and the wire are constructed so as to provide a frequency oscillator. The at least one magnet emits a magnetic field interacting with the wire. The viscometer can be any of the versions discussed above.

In yet another aspect, the down hole tool can be provided with a comparison chamber containing a fluid of known properties, e.g., viscosity and density. The down hole conditions, e.g., pressure and temperature, within the comparison chamber are similar (and preferably identical) to the down hole conditions within the evaluation cavity. The down hole tool is also provided with a sensor unit within the comparison chamber such that the down hole includes one sensor unit positioned within a fluid of unknown parameters within the evaluation cavity and the other sensor unit positioned with a fluid of known parameters within the comparison chamber. A signal indicative of at least two of the unknown parameters of the fluid (e.g., viscosity and density) within the evaluation cavity is then computed.

In a further aspect, the present invention relates to a method for measuring at least two unknown parameters of an unknown fluid within a well bore penetrating a formation having the fluid therein. In this method, a fluid communication device of the down hole tool is positioned in sealing engagement with a wall of the well bore. Fluid is then drawn out of the formation and into an evaluation cavity within the down hole tool. Data of the fluid within the evaluation cavity is sampled with a viscometer-densimeter having a wire positioned within the evaluation cavity and suspended between two connectors. The wire and the connectors are constructed to provide a frequency oscillator.

In this aspect, the evaluation cavity can be a flow-line or a sample chamber. With the data sampled by the viscometer-densimeter, at least two parameters can be calculated utilizing the data sampled within the evaluation cavity. The at least two parameters include viscosity and density.

In yet another aspect, the method can further comprise the step of sampling data with respect to a known fluid within a comparison chamber having a temperature and pressure related to the temperature and pressure of the fluid within the evaluation cavity. In this instance, the method typically further includes the step of calculating at least two parameters of the unknown fluid within the evaluation cavity utilizing the data sampled from the comparison chamber and the data sampled from the evaluation cavity.

In a further aspect, the present invention relates to a computer readable medium which can be either provided to or included in an analytical circuit for calculating at least two fluid parameters, such as the viscosity and density of the fluid. In this instance, the computer readable medium includes logic for (1) receiving feedback from at least two sensor units with one sensor unit positioned within a fluid of unknown parameters and the other sensor unit positioned with a fluid of known parameters, and (2) computing a signal indicative of at least two of the unknown parameters of the fluid in which the one sensor unit is positioned while substantially eliminating variations in the well bore conditions surrounding the sensor unit within the fluid of unknown parameters. The logic for computing the signal can include, for example, logic for performing a joint inversion of the data received from the sensor units.

In each of the aspects of the present invention recited above, the at least two fluid parameters are preferably calculated simultaneously.

BRIEF DESCRIPTION OF THE DRAWINGS

So that the above recited features and advantages of the present invention can be understood in detail, a more particular description of the invention, briefly summarized above, may be had by reference to the embodiments thereof that are illustrated in the appended drawings. It is to be noted, however, that the appended drawings illustrate only typical embodiments of this invention and are therefore not

FIG. 4 is a side elevation of a viscometer-densimeter positioned within an evaluation cavity.

FIG. 5 is a cross-sectional view of a sensor unit of the viscometer-densimeter of FIG. 4 showing a suspended wire.

DETAILED DESCRIPTION OF THE INVENTION

Figure 2:
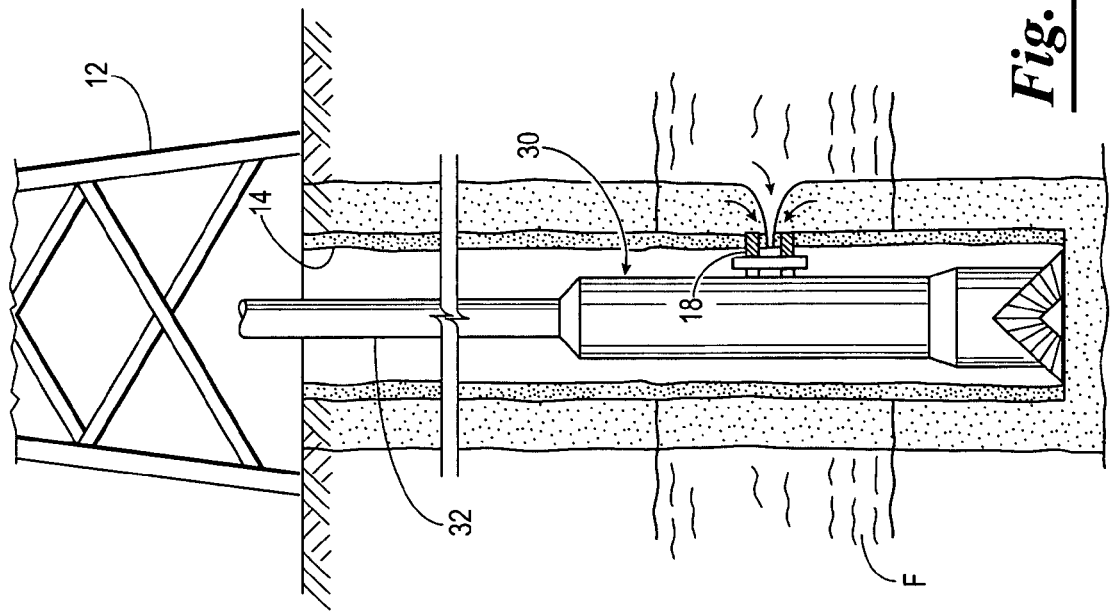
FIG. 2 is a schematic, partial cross-sectional view of a down hole drilling tool having an internal viscometer-densimeter with the down hole drilling tool suspended from a rig.

Presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic in the interest of clarity and conciseness.

DEFINITIONS

Certain terms are defined throughout this description as they are first used, while certain other terms used in this description are defined below:

"Annular" means of, relating to, or forming a ring, i.e., a line, band, or arrangement in the shape of a closed curve such as a circle or an ellipse.

"Contaminated fluid" means a fluid, e.g., gas or a liquid, that is generally unacceptable for hydrocarbon fluid sampling and/or evaluation because the fluid contains contaminates, such as filtrate from the mud utilized in drilling the bore hole.

"Down hole tool" means tools deployed into the well bore by means such as a drill string, wire line, and coiled tubing for performing down hole operations related to the evaluation, production, and/or management of one or more subsurface formations of interest.

"Operatively connected" means directly or indirectly connected for transmitting or conducting information, force, energy, or matter (including fluids).

"Virgin fluid" means subsurface fluid, e.g., gas or a liquid, that is sufficiently pure, pristine, connate, uncontaminated or otherwise considered in the fluid sampling and analysis field to be acceptably representative of a given formation for valid hydrocarbon sampling and/or evaluation.

"Fluid" means either "virgin fluid" or "contaminated fluid."

"Clamp" means a device designed to bind or constrict or to press two or more parts together so as to hold them firmly.

"Connector" means any device or assembly, such as a clamp, for rigidly joining or gripping a portion of a wire.

"frequency oscillator" means the resonant frequency of a tensioned wire in vacuum (hereinafter referred to as "$f_o$") is predictable so that changes in well bore conditions, e.g., temperature and pressure, do not have a substantial effect on the resonant frequency of the tensioned wire whereby readings obtained from the tensioned wire in varying well bore conditions are acceptably representative of the characteristics of the fluid interacting with the tensioned wire.

DETAILED DESCRIPTION

Figure 1:
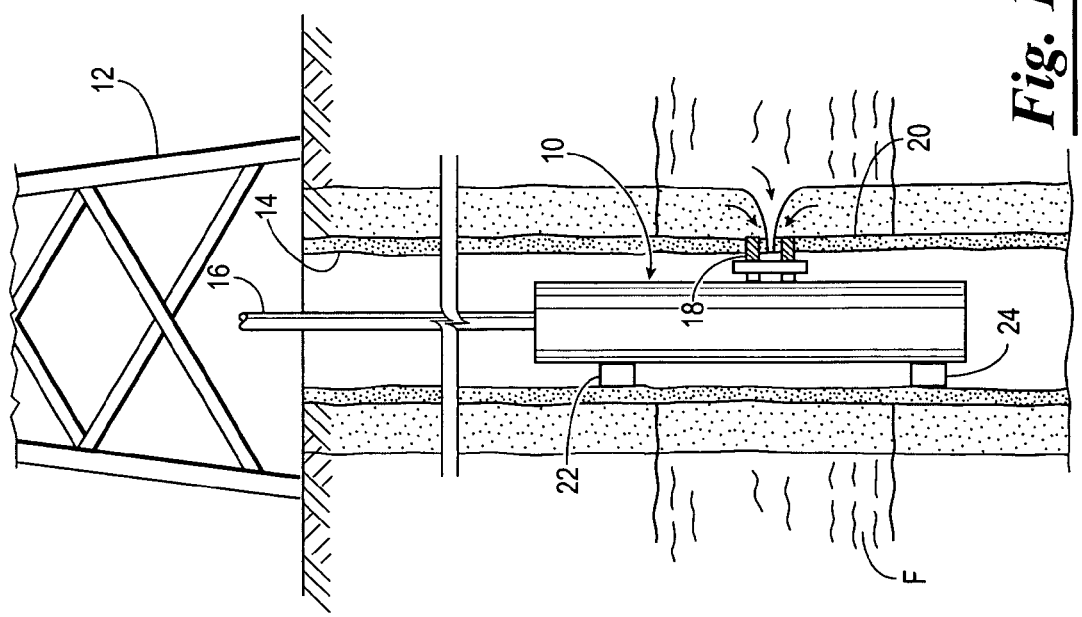
FIG. 1 is a schematic, partial cross-sectional view of a down hole wire line tool having an internal viscometer-densimeter with the wire line tool suspended from a rig.

FIG. 1 depicts a down hole tool 10 constructed in accordance with the present invention suspended from a rig 12 into a well bore 14. The down hole tool 10 can be any type of tool capable of performing formation evaluation, such as drilling, coiled tubing or other down hole tool. The down hole tool 10 of FIG. 1 is a conventional wire line tool deployed from the rig 12 into the well bore 14 via a wire line cable 16 and positioned adjacent to a formation F. The down hole tool 10 is provided with a probe 18 adapted to seal with a wall 20 of the well bore 14 (hereinafter referred to as a "wall 20" or "well bore wall 20") and draw fluid from the formation F into the down hole tool 10 as depicted by the arrows. Backup pistons 22 and 24 assist in pushing the probe 18 of the down hole tool 10 against the well bore wall 20.

FIG. 2 depicts another example of a down hole tool 30 constructed in accordance with the present invention. The down hole tool 30 of FIG. 2 is a drilling tool, which can be conveyed among one or more (or itself may be) a measurement-while-drilling (MWD) drilling tool, a logging-while-drilling (LWD) drilling tool, or other drilling tool that is known to those skilled in the art. The down hole tool 30 is attached to a drill string 32 driven by the rig 12 to form the well bore 14. The down hole tool 30 includes the probe 18 adapted to seal with the wall 20 of the well bore 14 to draw fluid from the formation F into the down hole tool 30 as depicted by the arrows. The viscometer-densimeters or sensor units described below can be used with either the down hole tool 10 or the down hole tool 30.

Figure 3A:
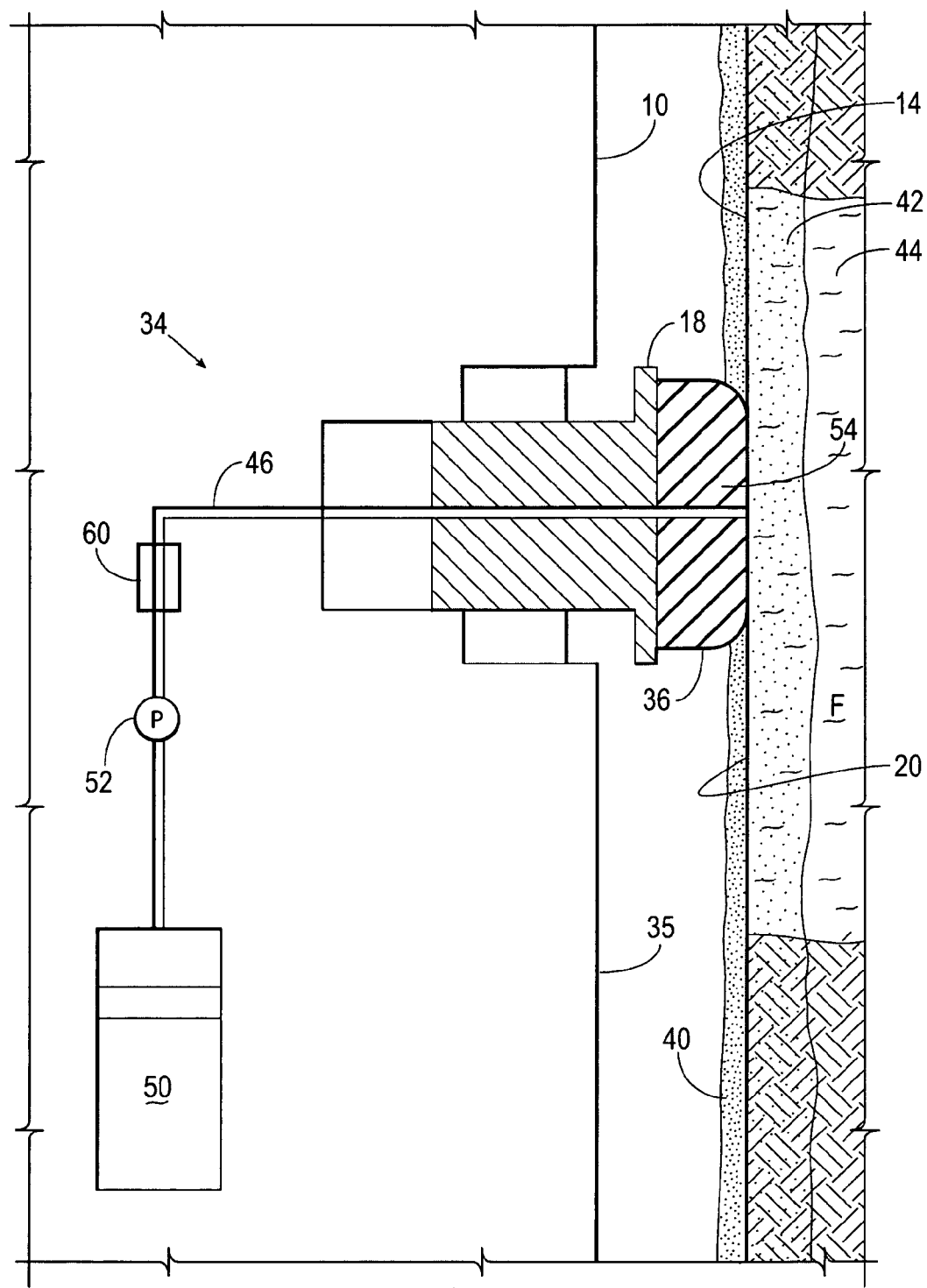
FIG. 3A is a schematic representation of a portion of the down hole tool of FIG. 1 having a probe registered against a sidewall of the well bore and a viscometer-densimeter positioned within an evaluation flow line within the down hole tool.

FIG. 3A is a schematic view of a portion of the down hole tool 10 of FIG. 1 depicting a fluid flow system 34. The probe 18 is preferably extended from a housing 35 of the down hole tool 10 for engagement with the well bore wall 20. The probe 18 is provided with a packer 36 for sealing with the well bore wall 20. The packer 36 contacts the well bore wall 20 and forms a seal with a mud cake 40 lining the well bore 14. The mud cake 40 seeps into the well bore wall 20 and creates an invaded zone 42 about the well bore 14. The invaded zone 42 contains mud and other well bore fluids that contaminate the surrounding formations, including the formation F and a portion of the virgin fluid 44 contained therein.

The probe 18 is preferably provided with an evaluation flow line 46. Examples of fluid communication devices, such as probes and dual packers, used for drawing fluid into a flow line are depicted in U.S. Pat. Nos. 4,860,581 and 4,936,139.

The evaluation flow line 46 extends into the down hole tool 10 and is used to pass fluid, such as virgin fluid 44 into the down hole tool 10 for testing and/or sampling. The evaluation flow line 46 extends to a sample chamber 50 for collecting samples of the virgin fluid 44. A pump 52 may be used to draw fluid through the flow line 46.

While FIG. 3A shows a sample configuration of a down hole tool used to draw fluid from a formation, it will be appreciated by one of ordinary skill in the art that a variety of configurations of probes, flow lines and down hole tools may be used and is not intended to limit the scope of the invention.

Figure 3B:
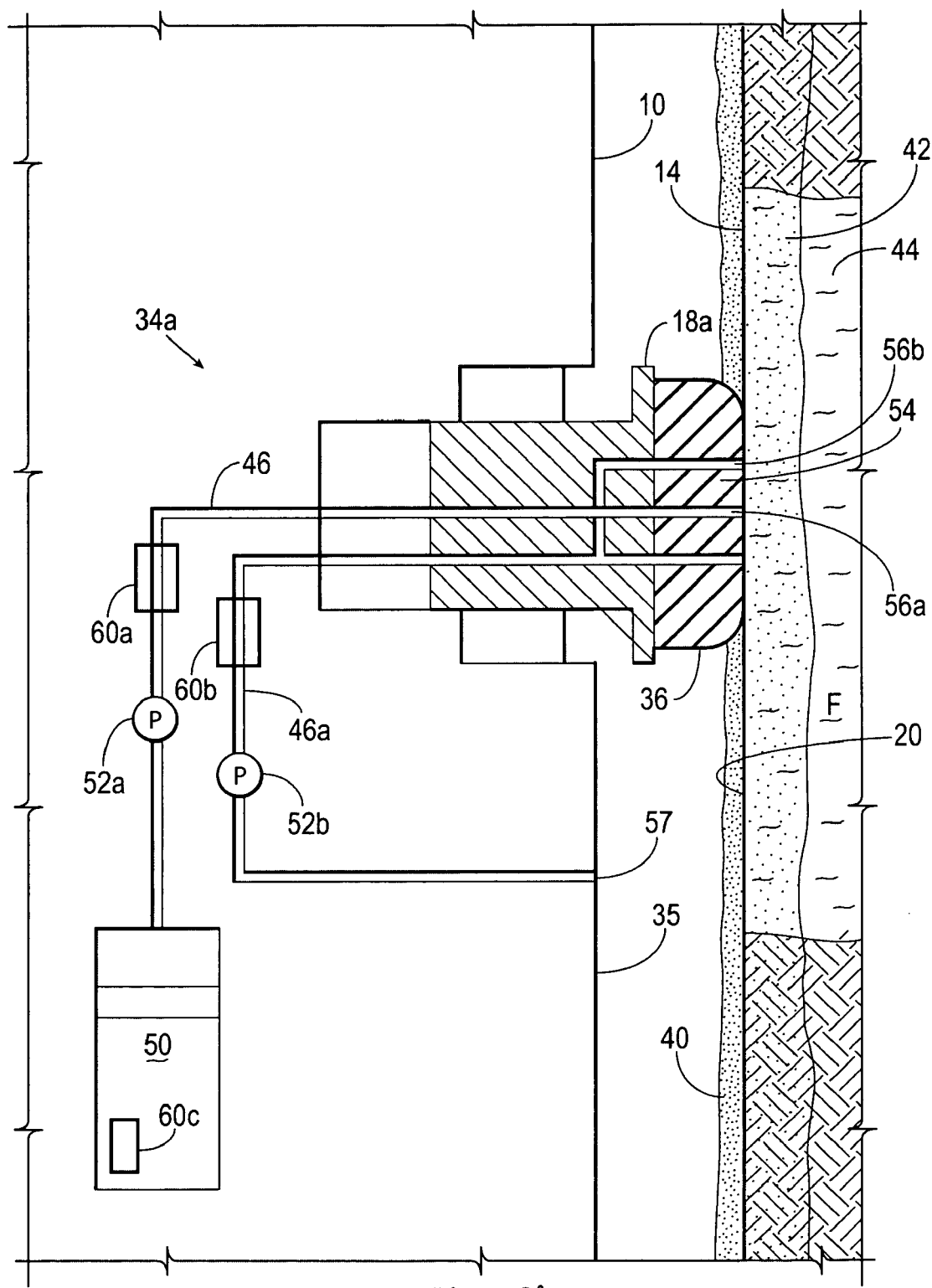
FIG. 3B is a schematic representation of another version of the down hole tool of FIG. 1 having a cleanup flow line utilized in combination with a dual packer.

For example, FIG. 3B is a schematic view of a portion of another version of the down hole tool 10 having a modified probe 18a and a fluid flow system 34a for drawing fluid into separate flow lines. More specifically, the fluid flow system 34a depicted in FIG. 3B is similar to the fluid flow system 34 depicted in FIG. 3A, except that the fluid flow system 34a includes a cleanup flow line 46a in addition to the evaluation flow line 46 as well as pumps 52a and 52b associated with the respective flow lines 46 and 46a. The probe 18a depicted in FIG. 3B is similar to the probe 18 depicted in FIG. 3A, except that the probe 18a has two separate cavities 56a and 56b with the cavity 56a communicating with the flow line 46 and the cavity 56b communicating with the flow line 46a. The cavity 56b extends about the cavity 56a such that the cavity 56b draws "contaminated fluid" from the formation F to permit the cavity 56a to draw "virgin fluid" from the formation F. The contaminated fluid is expelled from the cleanup flow line 46a into the well bore 14 through an outlet 57. Examples of fluid communication devices, such as probes and dual packers, used for drawing fluid into separate flow lines are depicted in U.S. Pat. No. 6,719,049 and US Published Application No. 20040000433, assigned to the assignee of the present invention, and U.S. Pat. No. 6,301,959 assigned to Halliburton.

In accordance with the present invention, a viscometer-densimeter 60 (a, b, c) is associated with an evaluation cavity within the down hole tool 10, such as the evaluation flow line 46, the cleanup flow line 46a, or the sample chamber 50 for measuring the viscosity of the fluid within the evaluation cavity. In the example depicted in FIG. 3B, the viscometer-densimeter 60 is labeled with the reference numerals 60a, 60b and 60c for purposes of clarity. The viscometer-densimeter 60 is shown in more detail in FIGS. 4, 5 and 6.

The down hole tool 30 may also provided with the housing, the probe, the fluid flow system, the packer, the evaluation flow line, the cleanup flow line, the sample chamber, the pump(s) and the viscometer-densimeter(s) in a similar manner as the versions of the down hole tool 10 depicted in FIGS. 3A and 3B.

Figure 6:
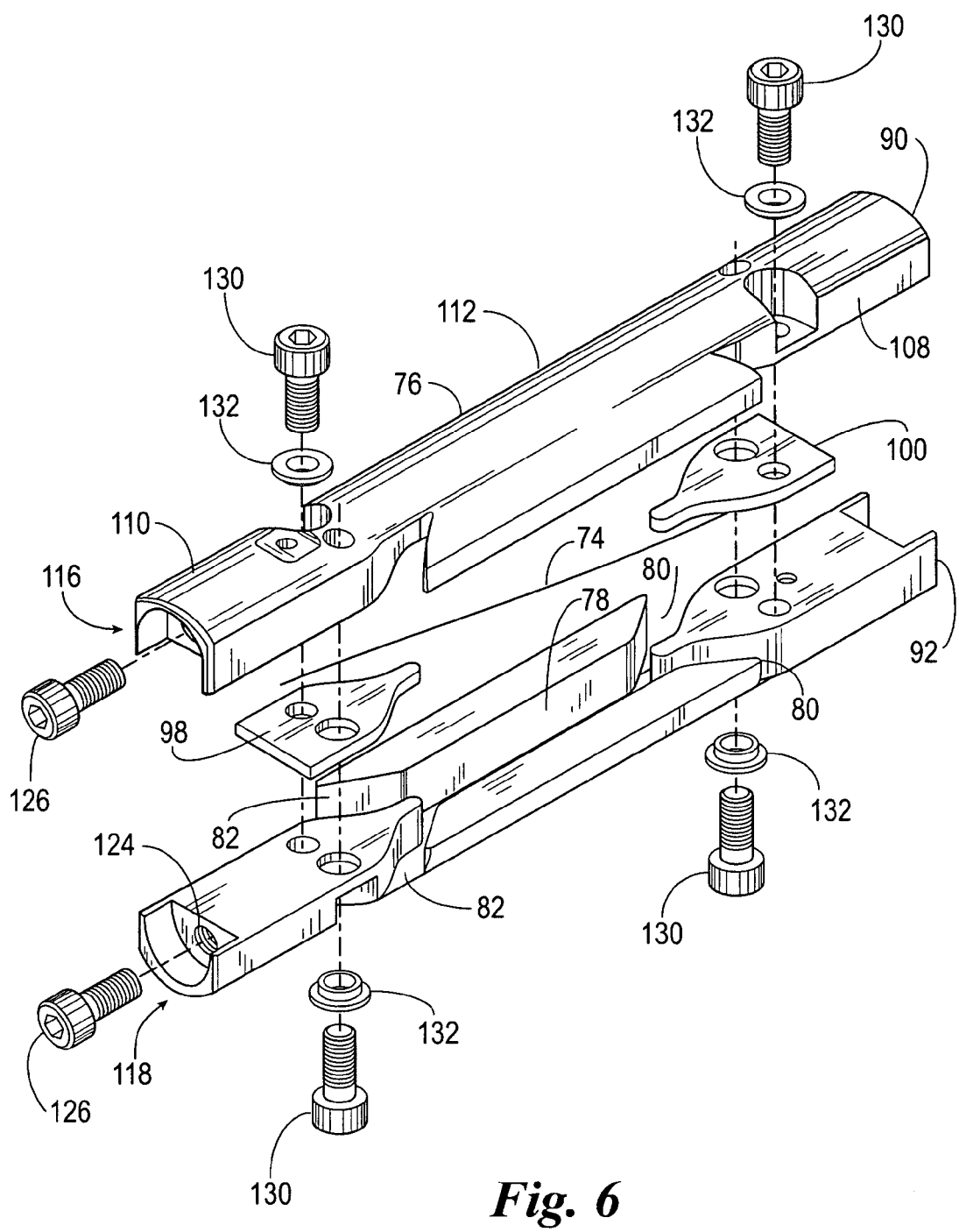
FIG. 6 is an exploded perspective view of the sensor unit of the viscometer-densimeter depicted in FIG. 4.

Referring now to FIGS. 4–6, the viscometer-densimeter 60 will be described in detail hereinafter with respect to the evaluation cavity being within the evaluation flow line 46. However, it should be understood that the following description is equally applicable to the evaluation cavity being within the cleanup flow line 46a or the sample chamber 50. It should also be understood that although the viscometer-densimeter 60 will be described in conjunction with the down hole tool 10, such description is equally applicable to the down hole tool 30. Moreover, while the viscometer-densimeter 60 is depicted in FIGS. 3A and 3B positioned along flow lines 46 and 46a, the viscometer-densimeter 60 may be positioned in various locations about the down hole tool 10 for measuring down hole parameters.

In general, the viscometer-densimeter 60 has a sensor unit 62, one or more magnets 64(a, b), a signal processor 66, and an analytical circuit 68. In the example shown in FIG. 4, the viscometer-densimeter 60 is provided with two magnets which are designated in FIG. 4 by the reference numerals 64a and 64b. The sensor unit 62 is provided with at least two spatially disposed connectors 72, and a wire 74 (FIG. 5) suspended between the least two connectors 72 such that the wire 74 is available for interaction with the fluid when the sensor unit 62 of the viscometer-densimeter 60 positioned within the down hole tool 10 and the down hole tool 10 is positioned within the subterranean formation F and receives the fluid from the formation F. The magnets 64a and 64b emit a magnetic field, which interacts with the sinusoidal current flowing through the wire 74. The signal processor 66 electrically communicates with the wire 74 via signal paths 75a and 75b. The signal paths 75a and 75b can be wire, cable or air-way communication links. The signal processor 66 provides a drive voltage forming a sinusoidal current to the wire 74, which typically causes the wire 74 to vibrate or resonate consistent with the signal provided thereto. Typically, the signal provided to the wire 74 from the signal processor 66 can be considered a swept frequency constant current signal wherein the frequency of the signal is changing in a predetermined manner.

The analytical circuit 68 receives feedback from the wire 74. The sinusoidal current flows through the wire 74 and when the frequency is close to that of a resonance, typically the lowest order mode, a detectable motional electromotive force ("emf") is generated. It is the drive voltage and the motional emf that are measured as a function of frequency over the resonance. Typically, the analytical circuit 68 receives feedback from the wire 74 indicative of the resonant frequency of the wire 74. Depending upon the viscosity of the fluid, the resonant frequency of the wire 74 changes in a predictable manner, which allows for the determination of the viscosity of the fluid. The manner in which the viscosity is determined from the feedback from the wire 74 will be discussed in more detail below. The analytical circuit 68 can be any type of circuit capable of receiving feedback from the wire 74 and calculating the viscosity of the fluid. Typically, the analytical circuit 68 will include a computer processor executing a software program stored on a computer readable medium such as a memory or a disk, for permitting the analytical circuit 68 to calculate the viscosity. However, it should be understood that in certain embodiments, the analytical circuit 68 could be implemented using analog, or other types of devices. For example, the analytical circuit 68 may include an analog-to-digital converter followed by a decoder for calculating the viscosity of the fluid. Although the analytical circuit 68 and signal processor 66 have been shown in FIG. 4 separately, it should be understood that the analytical circuit 68 and the signal processor 66 can be implemented in a single circuit, or implemented in separate circuits. Furthermore, although the analytical circuit 68 and the signal processor 66 are illustrated in FIG. 4 as being within the down hole tool 10, it should be understood that the signal processor 66 and/or the analytical circuit 68 could be located external to the down hole tool 10. For example, the signal processor 66 for generating the swept signal can be located within the down hole tool 10, while the analytical circuit 68 is located outside of the well bore 14 in a monitoring center located either near the well bore 14 or remote from the well bore 14.

The sensor unit 62 of the viscometer-densimeter 60 is also provided with a housing 76. The housing 76 defines a channel 78 (FIGS. 5 and 6), an inlet 80 communicating with the channel 78, and an outlet 82 communicating with the channel 78. In the example depicted in FIG. 4, the fluid is flowing in a direction 84 through the evaluation flow line 46. Thus, when the fluid encounters the sensor unit 62, the fluid flows through the inlet 80, into the channel 78 and exits the housing 76 through the outlet 82. When the housing 76 is provided with an outer dimension smaller than an inner dimension of the evaluation flow line 46, a certain amount of the fluid will also flow past the housing 76 in a channel 87 (FIG. 4) formed between an outer surface 88 of the housing 76, and an inner surface 89 of the evaluation flow line 46.

The wire 74 is positioned within the channel 78 so that the fluid will come into contact with substantially the entire wire 74 between the connectors 72 as the fluid passes through the housing 76. This ensures that the fluid flows over the entire length of the wire 74 between the connectors 72 to facilitate cleaning the wire 74 between fluids. The wire 74 is constructed of a conductive material capable of vibrating at a plurality of fundamental mode resonant frequencies (or harmonics thereof) depending upon the tension of the wire 74 and the viscosity of the fluid surrounding the wire 74. The wire 74 is desirably constructed of a material having a large density because the greater the difference in density of the wire 74 to that of the fluid the greater the sensitivity. The wire 74 also needs to have a high Young's modulus to provide a stable resonance while the density provides sensitivity to the fluid around it, through the ratio of the density of the fluid to the density of the wire A variety of materials can be used for the wire 74. For example, the wire 74 can be constructed of Tungsten or Chromel. When the wire 74 is used for sensing a gas, such as natural gas, it is preferred that the wire 74 have a relatively smooth outer surface. In this instance Chromel is a preferred material for constructing the wire 74.

As shown in FIG. 4, the magnets 64 are preferably positioned on the exterior of the evaluation flow line 46 and mounted to an exterior surface of the evaluation flow line 46. The magnets 64 can also be incorporated into the housing 76. Alternatively, the housing 76 can be constructed of a magnetic material.

As shown in FIGS. 5 and 6, the housing 76 may be provided with a first housing member 90 and a second housing member 92. The first housing member 90 and the second housing member 92 cooperate to define the channel 78. The first housing member 90 and the second housing member 92 are preferably constructed of a conductive, non-magnetic material such that the magnetic field generated by the magnets 64 can interact with the wire 74 without substantial interference from the housing 76. For example, the first housing member 90 and the second housing member 92 may be constructed of a down hole compatible material, such as K500 Monel, tungsten or another type of non-magnetic material, e.g., stainless steel.

The housing 76 is also provided with an insulating layer 96 (FIG. 5) positioned between the first housing member 90 and the second housing member 92 so as to electrically isolate the first housing member 90 from the second housing member 92. The wire 74 extends between opposite sides of the insulating layer 96 to electrically connect the first housing member 90 to the second housing member 92. The insulating layer 96 may be constructed of a first insulating member 98, and a second insulating member 100. The wire 74 is provided with a first end 102, and a second end 104. The first insulating member 98 is positioned adjacent to the first end 102 of the wire 74, and the second insulating member 100 is positioned adjacent to the second end 104 of the wire 74. The wire 74 spans the channel 78 and serves to electrically connect the first housing member 90 to the second housing member 92.

In the example of the sensor unit 62 depicted in FIG. 4, each of the first housing member 90 and the second housing member 92 can be characterized as having a first end portion 108, a second end portion 110, and a medial portion 112 positioned between the first end portion 108 and the second end portion 110. The first end portion 108 and the second end portion 110 are provided with a cross-sectional area, or diameter which is less than a cross-sectional area or diameter of the medial portion 112. Thus, each of the first housing member 90, and the second housing member 92 has a shoulder 114 separating the first end portion 108 and the second end portion 110 from the medial portion 112. The inlet 80 and the outlet 82 are defined in the first housing member 90 and the second housing member 92 proximate to the shoulders 114 such that the channel 78 extends through the medial portion 112 of the housing 76. The shoulders 114 are shaped to direct the fluid into the inlet 80.

To connect the signal paths 75*a* and 75*b* to the sensor unit 62, the viscometer-densimeter 60 is further provided with a first terminal 116 coupled to the first housing member 90 and a second terminal 118 coupled to the second housing member 92. The signal processor 66 and the analytical circuit 68 are thus in communication with the first and second terminals 116 and 118 via the signal paths 75*a* and 75*b*. It should be noted that the signal paths 75*a* and 75*b* typically extend through the evaluation flow line 46 via one or more feed-throughs 120. The feed-throughs 120 provide a fluid tight seal to permit the signal paths 75*a* and 75*b* to extend through the evaluation flow line 46 while preventing fluid from flowing through the opening formed in the evaluation flow line 46.

The first terminal 116 and the second terminal 118 may be identical in construction and function. To implement the first terminal 116 and the second terminal 118, the first housing member 90 and the second housing member 92 can be provided with threaded holes 124 formed in either the first end portion 108 or the second end portion 110 of the first housing member 90 and the second housing member 92. In the example depicted in FIG. 5, the first housing member 90 and the second housing member 92 are provided with the threaded holes 124 formed in both the first end portion 108 and the second end portion 110 thereof. As depicted in FIGS. 4–6, the first terminal 116 and the second terminal 118 are also provided with threaded fasteners 126 to connect each of the signal paths 75a and 75b to the first housing member 90 and the second housing member 92.

The first housing member 90 and the second housing member 92 are connected together by way of any suitable mechanical or chemical type assembly. As depicted in FIG. 6, the viscometer-densimeter 60 is provided with a plurality of threaded fasteners 130 (FIG. 6) for securing the first housing member 90 to the second housing member 92. It should be noted that the threaded fasteners 130 are typically constructed of conductive materials, such as steel or aluminum. To prevent the threaded fasteners 130 from forming electrical paths between the first housing member 90 and the second housing member 92, the viscometer-densimeter 60 is also provided with a plurality of electrically insulated feedthroughs 132 to electrically isolate each of the threaded fasteners 130 from one of the corresponding first housing member 90 and the second housing member 92.

The sensor unit 62 of the viscometer-densimeter 60 can be anchored within the evaluation flow line 46 by any suitable assembly. It should be understood that the sensor unit 62 should be anchored to prevent longitudinal movement within the evaluation flow line 46 and rotational movement within the evaluation flow line 46. The signal paths 75a and 75b are preferably provided with sufficient rigidity to prevent longitudinal and/or rotational movement of the sensor unit 62 within the evaluation flow line 46. Further anchoring means can also be used to prevent movement of the sensor unit 62 within the evaluation flow line 46. For example, the evaluation flow line 46 can be necked-down downstream of the sensor unit 62 so as to prevent longitudinal movement of the sensor unit 62 within the evaluation flow line 46.

As will be understood by one skilled in the art, the first housing member 90 and the second housing member 92, when secured together by way of the threaded fasteners 130, cooperate to form the connectors 72. The wire 74 is connected and tensioned as follows. The wire 74 is connected at one end. The other end is fed through the second connector 72 but is not tightened. A mass (not shown) is attached from the end protruding from the loose connector 72. The magnitude of the mass, which hangs from the wire 74 within the Earth's gravitational field, determines the tension for a wire diameter and therefore the resonance frequency; a resonance frequency of about 1 kHz can be obtained with a mass of 500 g suspended on a wire of diameter 0.1 mm. The diameter of the wire 74 can be varied to change the viscosity range to be measured. After about 24 h, the wire 74 is clamped at the second end and the mass removed. This procedure reduces the twist within the wire 74. The wire 74 is then heated and cooled so as to produce a wire with a resonance frequency that is reasonably stable between each thermal cycle; for the viscometer-densimeter 60, the wire 74 resonance frequency needs to be stable during the time required to determine the complex voltage as a function of frequency over the resonance which is on the order of 60 s.

To calculate the viscosity, a sinusoidal current is fed through the wire 74 in the presence of a magnetic field. The magnetic field is perpendicular to the wire 74 and in the presence of the sinusoidal current causes the wire 74 to move. The resulting induced electromotive force (motional emf) or complex voltage is added to the driving voltage. The motional emf can be detected via the analytical circuit 68 with signal processors that include lock-in amplifiers, where the driving voltage can be offset or rendered null, or spectrum analyzers. When the frequency of the current is close to or at that of the fundamental resonance frequency the wire 74 resonates. The complex voltage is usually measured at frequencies over the resonance and the observations combined with the working equations, wire density and radius, to determine the viscosity for a fluid of known density. The magnitude of the current depends on the viscosity of the fluid and is varied so that an acceptable signal-to-noise ratio is obtained with the detection circuitry; values less than 35 mA are typically used and the resulting complex motional emf of a few microvolts. In addition to the magnitude of the current, the diameter of the wire 74 also determines the upper operating viscosity; increasing the wire diameter increases the upper operating viscosity. There are other ways of exciting and detecting wire motion but none so convenient as a lock-in amplifier.

To calculate the viscosity and density of the fluid from the feedback received from the wire 74, the analytical circuit 68 operates as follows. The wire 74 is placed in a magnetic field and driven in steady-state transverse oscillations by passing an alternating current through it. The resulting voltage V developed across the wire is composed of two components:

$$V = V_1 + V_2, \text{ and} \tag{1}$$

The first term, $V_1$, arises simply from the electrical impedance of the stationary wire while the second, $V_2$, arises from the motion of the wire in the presence of the magnetic field. $V_1$ is represented by $$V_1 = a + i(b + cf), \tag{2}$$

In equation (2), f is the frequency at which the wire 74 is driven in the presence of a magnetic field, while a, b and c are adjustable parameters that are determined by regression with experimental results. The parameters a, b and c account for the electrical impedance of the wire and also absorb the offset used in the lock-in amplifier to ensure the voltage signal is detected at the most sensitive range possible. The second component of $V_2$ is given in the working equation of the instrument by $$V_2 = \frac{\Lambda f_1}{f_0^2 - (1+\beta)f^2 + (\beta' + 2\Delta_0)f^2 i}. \tag{3}$$

In equation (3), A is an amplitude, $f_0$ the resonance frequency of the wire in vacuum, $A_0$ the internal damping of the wire, $\beta$ the added mass arising from the fluid displaced by the wire, and $\beta'$ the damping due to the fluid viscosity.

The fluid mechanics of a vibrating wire that revealed the added mass of the fluid, $\beta$, and viscous drag, $\beta'$, can be represented by $$\beta = k \frac{\rho}{\rho_s}, \text{ and} \tag{4}$$

$$\beta' = k' \frac{\rho}{\rho'_s}, \tag{5}$$

where k and k' are given by $$k = -1 + 2\Im(A), \text{ and} \tag{6}$$

$$k' = 2\Re(A). \tag{7}$$

In equations (6) and (7), A is a complex quantity given by $$A = i\left\{1 + \frac{2K_1(\sqrt{\Omega i})}{\sqrt{\Omega i}\, K_0(\sqrt{\Omega i})}\right\},\tag{8}$$

where $$\Omega = \frac{\omega \rho R^2}{\eta}.\tag{9}$$

In equation (8), $K_0$ and $K_1$ are modified Bessel functions and $\Omega$ is related to the Reynolds number that characterizes the flow around the cylindrical wire or radius R. In equation (9), the fluid viscosity and density are given by $\eta$ and $\rho$, respectively. Thus, the viscosity and density of a fluid can be determined by adjusting the values so that in-phase and quadrature voltages predicted from equations (1) through (9) are consistent with experimentally determined values over a function of frequency. The frequency range over which data is collected is typically about $f_r \pm 5g$ where g is the half-width of the resonance curve and $f_r$ is the fundamental transverse resonance frequency. In an electrically perfect apparatus where the signal-to-noise ratio is large and electrical cross-talk, which increases with increasing frequency, zero the band-width selection is not critical. However, this is critical when the $Q\{=f/(2g)\}$ tends to unity that occurs when the band-width increases, which it does with increasing viscosity, and, unless the drive current increased, a corresponding decrease in signal-to-noise ratio; the importance of determining the band-width over which measurements are performed will become apparent below.

Equations (4) through (9) are obtained by assuming the following: (1) the radius of the wire 74 is small in comparison with the length of the wire 74, (2) the compressibility of the fluid is negligible, (3) the radius of the housing 76 containing the fluid is large in comparison to the wire radius so that the boundary effects are negligible, and (4) the amplitude of oscillation is small. In the vibrating wire viscometers reported in the literature, the resonant frequency is sensitive to both the tension in the wire and the density of the fluid that surrounds it; this sensitivity to density is often increased by clamping the wire at the top and mounting a mass on the lower end thus invoking Archimedes principle. However, if the density is determined from an alternative source, for example, an equation of state, only the resonance line width need be stable.

In general, the vibrating wire viscometer, such as the viscometer-densimeter 60, is an absolute device that, in theory, requires no calibration constants to be determined. However, in practice some physical properties of the wire 74 such as density and radius cannot be determined to sufficient accuracy by independent methods; hence, those properties are usually determined by calibration. To do this, measurements are made in both vacuum and a fluid for which the viscosity and density are known. The former yields $\Delta_0$. The wire radius, R, is the only other unknown variable required to perform viscosity measurements. The wire radius can be determined in a single measurement given the viscosity and density of the calibration fluid.

1. Modification of Working Equations

The complex voltages V developed across the wire 74 consists of $V_1$ arising from the electrical impedance of the wire 74 and $V_2$ arising from the motion of the wire 74 in the presence of the magnetic field (Equation 1). Other than the contribution from electrical impedance, $V_1$ also accounts for background noise such as electrical cross-talk or other forms of coupling. These interference gives rise to a relatively smooth background over the frequency interval near the resonant frequency of the vibrating wire 74. In order to adequately replicate the measured complex voltages as a function of frequency, an additional frequency-dependent parameter is included in Equation (2), i.e.

$$V_1 = a + bf + i(c + df).\tag{10}$$

Without taking the additional frequency-dependent term in Equation (10) into account, the measured complex voltages are often not fitted well with the working equations and consequently, significant errors in fluid density and viscosity are incurred. This is particularly true for high viscosity fluids.

2. Determination of Fluid Density and Viscosity from Vibrating Wire

Determination of fluid density and viscosity requires data fitting with the working equations of the vibrating wire 74. The method of least squares fitting is based on the idea that the optimum characterization of a set of data is one that minimizes the sum of the squares of the deviation of the data from the fitting model (or working equations). The sum of squares of the deviation is closely related to the goodness-of-fit statistic called chi-square (or $\chi^2$ $$\chi^2 = \frac{\sum_{i=1}^{N} |D(f_i) - V(f_i)|^2}{\nu},\tag{11}$$

where $f_i$ is the frequency index, $D(f_i)$ and $V(f_i)$ are the recorded complex voltages and the working equations, respectively, and $\nu$ is the number of degrees of freedom for fitting N data points. The least squares criterion is formulated as finding the unknown parameters, including the fluid density and viscosity, to minimize the chi-square measure defined in (11), i.e.

$$\min_{\rho,\eta,f_0,\Lambda,a,b,c,d}\chi^2,\tag{12}$$

where "$\rho$", "$\eta$", "$f_0$", "$\Lambda$", "a", "b", "c" and "d" are the unknown parameters. The Levenberg-Marquardt algorithm [14] provides a nonlinear regression procedure to solve this minimization problem.

Among all the unknown parameters, the oscillating amplitude (i.e. $\Lambda$) and the constants related to electrical impedance of the stationary wire and other background interference (i.e. a, b, c and d) are well determined by the minimization procedure. However, a fundamental uncertainty among the density, viscosity and $f_0$ prevents the fitting itself from sorting out the correct density and viscosity values. In order to exterminate this fundamental uncertainty, additional relationships among the density, viscosity and $f_{0a}$ are used as constraints in the fitting procedure. Mathematically, a relationship among these variables can be written in a general functional form $$G(\rho,\eta,f_0)=0\tag{13}$$

Alternatively, the relationship may also include additional measurements such as the half-width of the resonance (g) and the resonant frequency ($f_r$) that can be derived from the data $$H(\rho,\eta,f_0,g,f)=0. \quad (14)$$

Equations (13)–(14) can be established experimentally through calibration procedures or empirically based on field data. Our preferred embodiment here is a special case of Equations (13)–(14); specifically, a hyper plane defined by a fixed $f_0$. As discussed in Retsina et al. (Retsina, T.; Richardson, S. M.; Wakeham, W. A., *Applied Scientific Research*, 1987, 43, 325–346; and Retsina, T.; Richardson, S. M.; Wakeham, W. A., 1986, 43, 127–158) $f_0$ can be designated as the resonant frequency of the wire 74 in vacuum that is directly related to the tension exerted on the wire 74. If $f_0$ is known or given, one can limit the minimum search on the hyper plane defined by the fixed $f_0$.

Figure 7A:
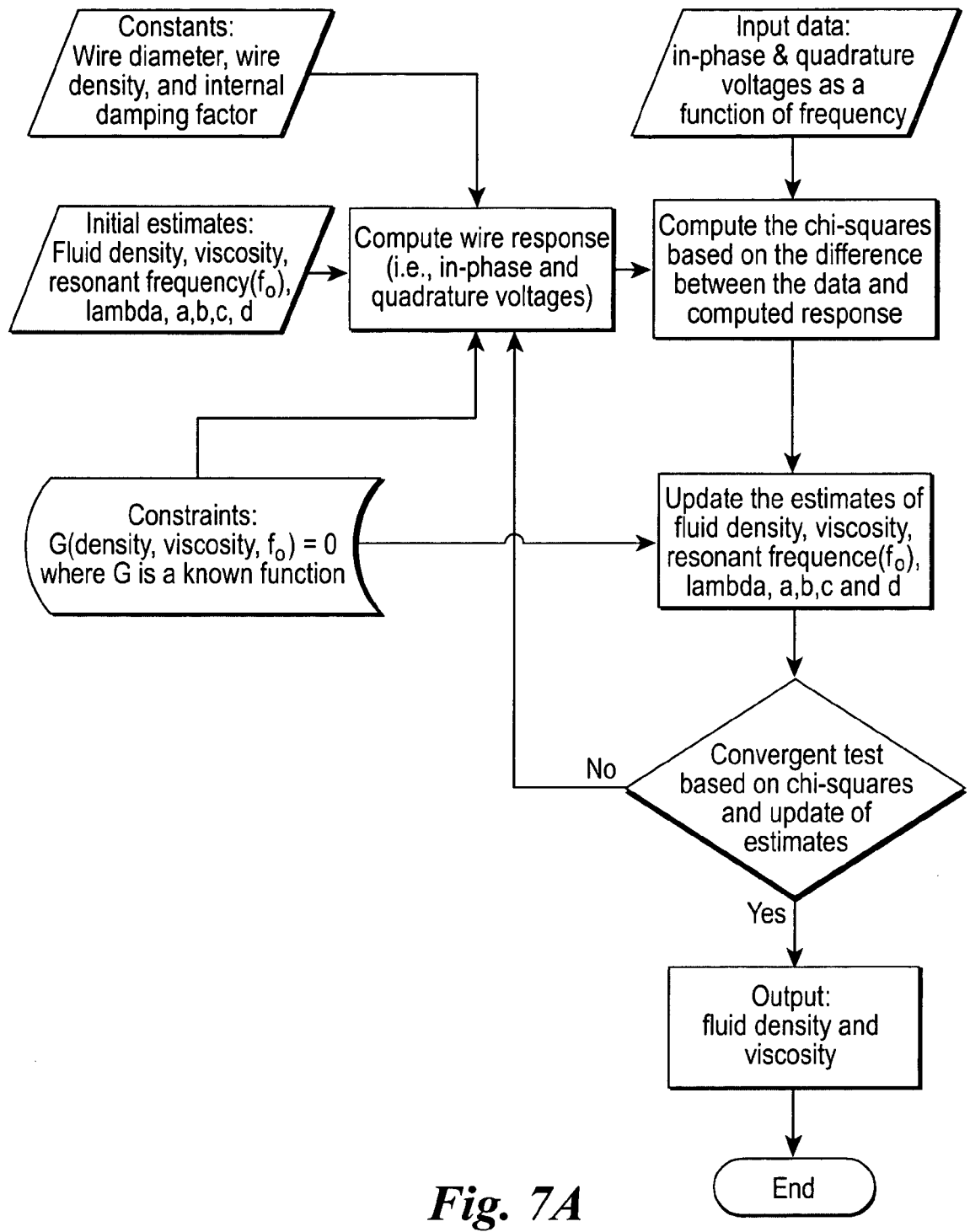
FIG. 7a is a logic flow diagram illustrating a method for simultaneously calculating viscosity and density.

FIG. 7a shows a flow chart 134 for calculating the viscosity and density simultaneously as discussed above. Initially, as indicated by block 134a, b and c, the constants for wire diameter, wire density, and internal damping factor; initial estimates for fluid density, viscosity, and resonant frequency $f_0$; as well as constraints G (density, viscosity, and resonant frequency $f_0$); are input into a computation block 134d. An initial wire response is then computed as represented by the block 134d. The initial wire response can be calculated in in-phase and quadrature voltages.

Input data, such as in-phase and quadrature voltages as a function of frequency are then received as indicated by a block 134e and the chi-squares are then computed based on the difference between the data and computed response as indicated by a block 134f. An update of the estimates of fluid density, viscosity, and resonant frequency, lambda, a, b, c and d are then received. Any non-linear regression analysis can be used to provide the updates as indicated by a block 134g. The analytical circuit 68 then applies a convergent test (as indicated by a block 134h) based on the chi-squares and the update of the estimates. If the convergent test indicates convergence within a predetermined or acceptable amount, the process branches to a step 134i where the fluid density and viscosity are output. However, if the convergent test indicates convergence outside the predetermined amount, the process branches back to the step 134d where the wire response is re-calculated based on the updated fluid density, viscosity and resonant frequency and the steps 134d, 134e, 134f, 134g and 134h are repeated until the convergence test indicates convergence within the predetermined amount.

Figure 7B:
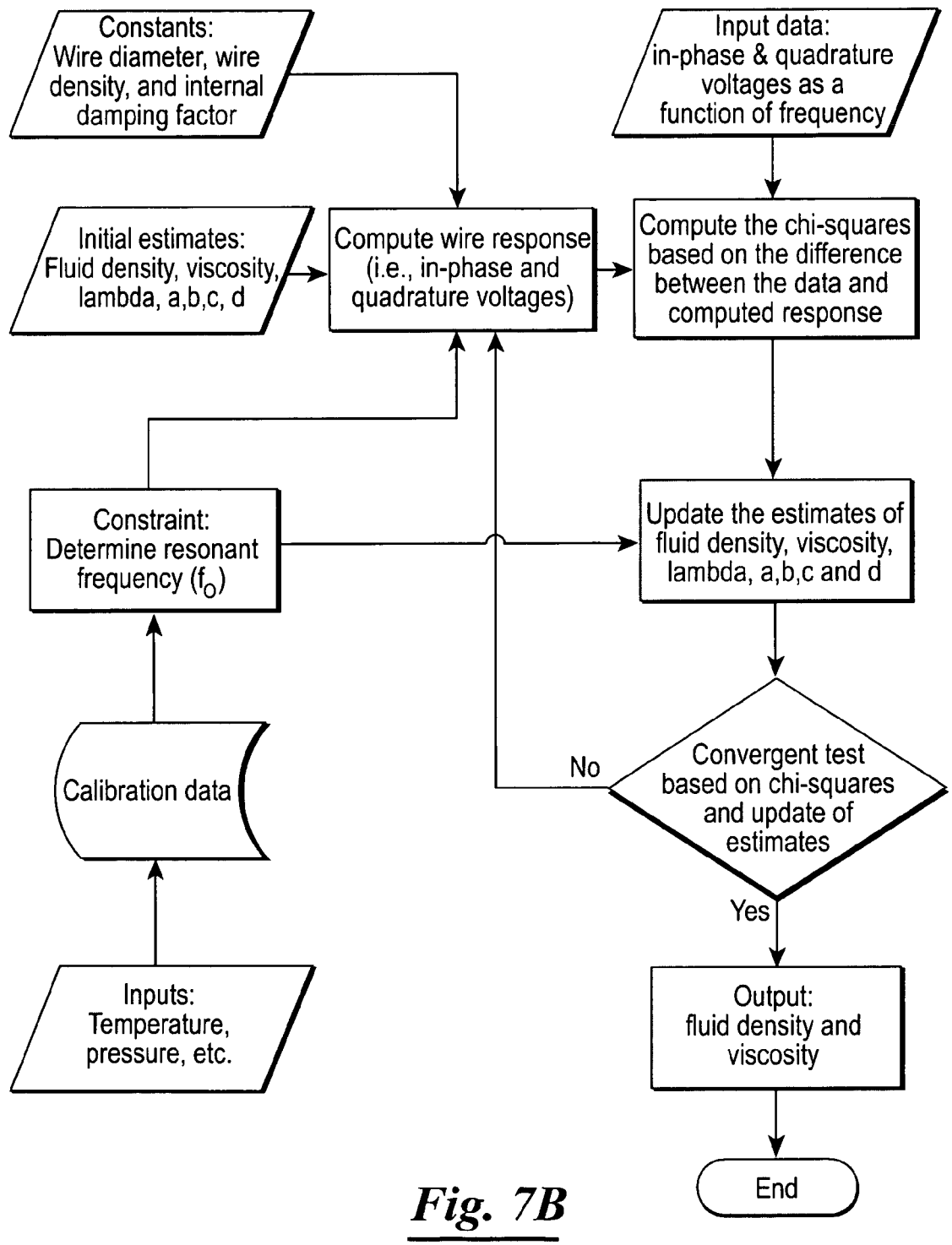
FIG. 7b is a logic flow diagram illustrating another method for simultaneously calculating viscosity and density.

FIG. 7b shows a flow chart 136 for calculating the viscosity and density simultaneously, in a manner exactly as described above with respect to FIG. 7a, with the following exceptions. It should be noted that steps in FIG. 7b which are identical to those in FIG. 7a have been labeled with identical reference numerals for purposes of clarity.

In the process for calculating the viscosity and density represented in FIG. 7b, the sensor unit 62 is tested to determine the resonant frequency $f_0$. To calibrate the sensor unit 62, the sensor unit 62 is placed in an environmental chamber with a known fluid, and then the temperature and pressure are varied so as to provide calibration data. The calibration data is then input into the analytical circuit 68 as indicated by a block 136b and such calibration data is utilized to compute the resonant frequency $f_0$ as indicated by a block 136c.

Figure 8:
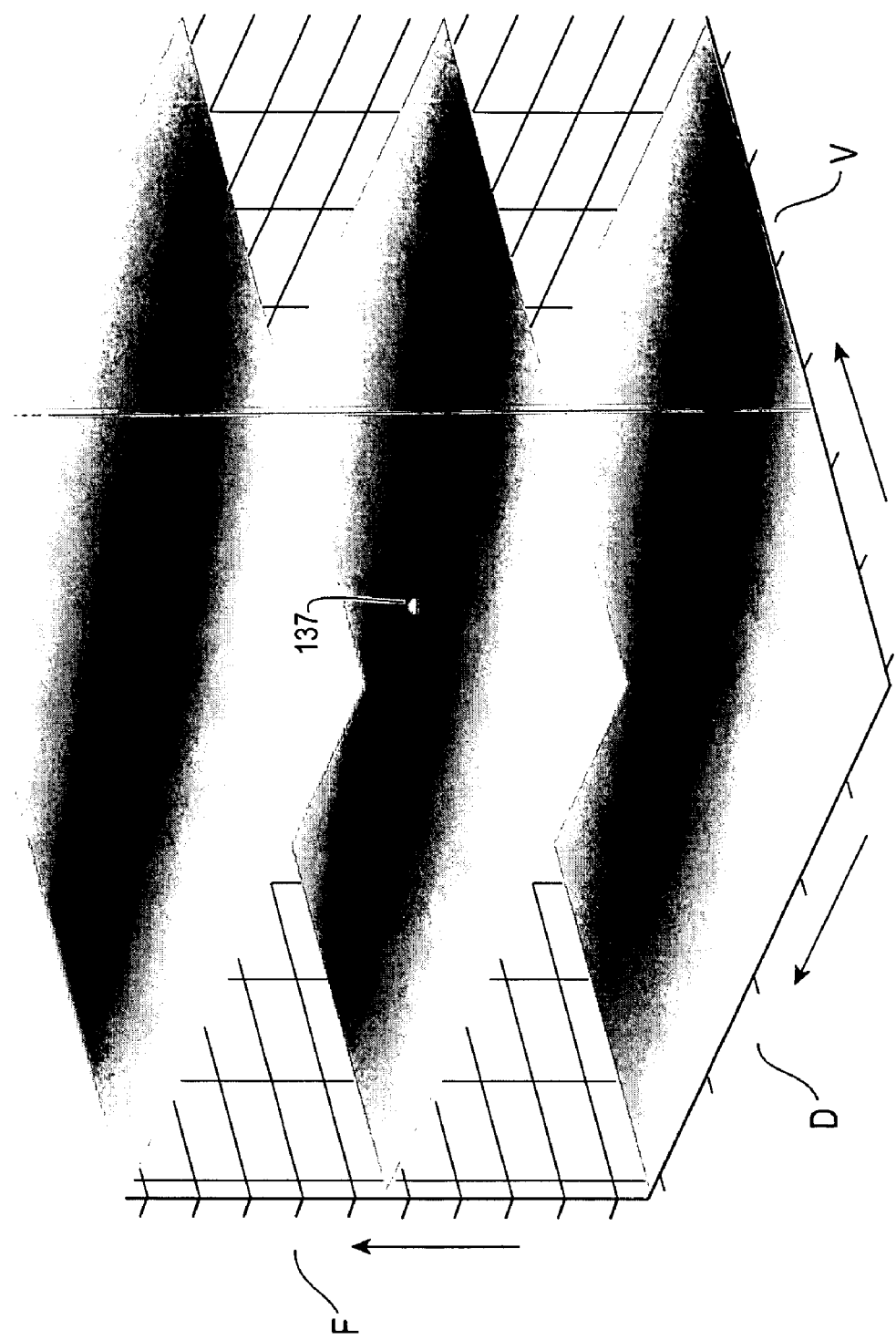
FIG. 8 is a graph illustrating a chi-square performance surface intercepted by a fixed-$f_0$ hyper plane showing a minimum utilized in the calculation of the density and viscosity.

FIG. 8 is a graph showing the chi-square performance surface intercepted by the fixed-$f_0$ hyper plane, where there is a global minimum. The graph includes axes F, D and V.

The F axis represents the frequency of $f_0$ in Hz. The D axis represents the density of the fluid surrounding the wire 74 in kg/m³. The V axis represents the viscosity of the fluid surrounding the wire 74 in cp. The meaning of the shading is the value of the Chi-square—the dark colors mean a lower chi-square value. The location of a minimum 137 provides the density and viscosity estimates.

If $f_0$ is stable and known within ±1 Hz, the fluid density can be determined within 3–4% for a wide range of fluids. The error is smaller (1–2%) for high viscosity fluids. If known within ±0.5 Hz, the density error reduces to about 1–2% for a wide range of fluids. The error in viscosity is generally smaller than the density error (about 3%) if $f_0$ is within ±1 Hz. Similarly, the error in viscosity is smaller for high viscosity fluids. To simultaneously estimate the fluid density and viscosity, the preferred embodiment requires a sensor unit forming a frequency oscillator for providing a stable and predictable $f_0$ in a wide variety of different temperatures and pressures. Typical temperature and pressure ranges in a down hole environment range from 50 to 200 degrees C. and 2.07 to 172.4 MPa (300 to 25000 psi).

Figure 9:
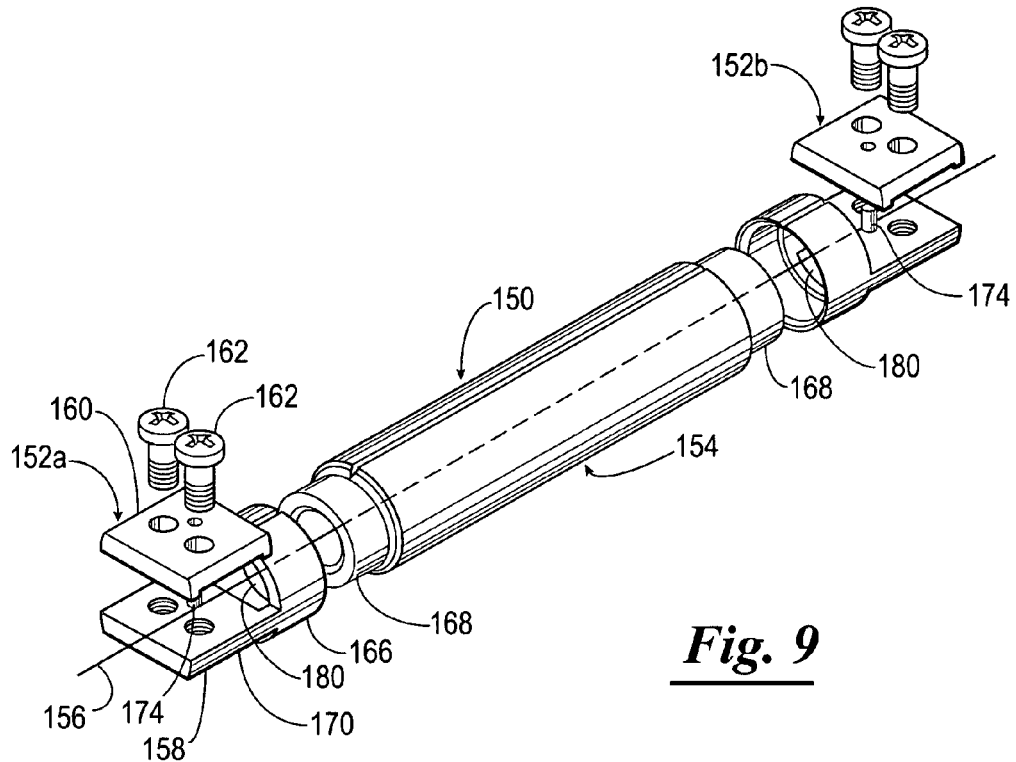
FIG. 9 is an exploded perspective view of another sensor unit of a viscometer-densimeter.
Figure 10:
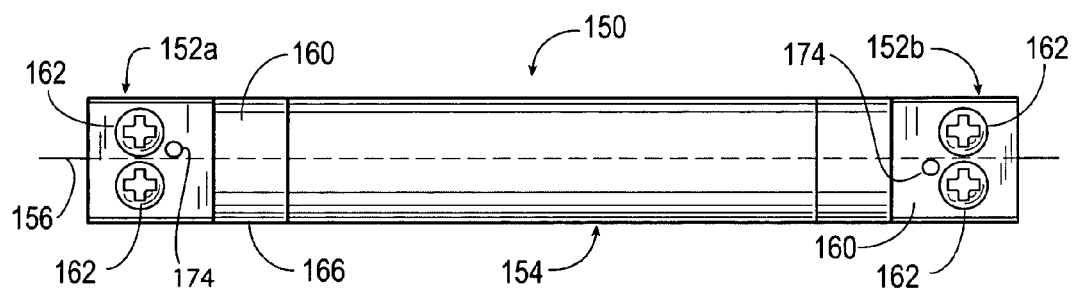
FIG. 10 is a top plan view of the sensor unit depicted in FIG. 9.

Shown in FIG. 9 is another version of a sensor unit 150 for use with the viscometer-densimeter 60. As will be discussed in more detail below, the sensor unit 150 is similar in construction and function as the sensor unit 62 described above, with the exception that the sensor unit 150 is provided with a pair of conductive connectors 152 separated by an insulating flow tube 154 surrounding a wire 156, rather than having the conductive first housing member 90 and second housing member 92 separated by a parallel extending insulating layer 96. The sensor unit 150 will be described in more detail below.

The sensor unit 150 forms a frequency oscillator for providing a stable and predictable $f_0$ so that at least two different parameters, such as density and viscosity of the fluid in which the sensor unit 150 is immersed can be calculated simultaneously from the data generated by the sensor unit 150.

The connectors 152 are designated in FIG. 9 by way of the reference numerals 152a 152b for purposes of clarity. The connectors 152 are identical in construction and function. Thus, only the connector 152a will be described hereinafter. The connector 152a is provided with a clamp member 158, a clamp plate 160, and at least one fastener 162 for connecting the clamp plate 160 to the clamp member 158. The clamp member 158 is connected to the flow tube 154 via any suitable mating assembly. For example, as shown in FIG. 9, the clamp member 158 is provided with an end support 166 that mates with a predetermined portion of the flow tube 154 such that the end support 166 is supported by the flow tube 154. In the version depicted in FIG. 9, the flow tube 154 is provided with a necked down portion 168, and the end support 166 defines a collar positioned over the necked down portion 168. The clamp member 158 is also provided with a flange 170 connected to and extending from the end support 166. To center the wire 156 on the flange 170, at least one registration pin 174 is provided on the flange 170. Desirably, the clamp member 158 is provided with at least two spaced-apart registration pins 174 such that the wire 156 can be threaded between the registration pins 174 as shown in FIG. 9.

The fasteners 162 connect the clamp plate 160 to the clamp member 158 so as to clamp the wire 156 thereto. The fasteners 162 can be any type of device capable of connecting the clamp member 158 to the clamp plate 160. For example, the fastener 162 can be a screw.

The flow tube 154 is preferably constructed of a material which has a similar coefficient of thermal expansion as the wire 156. When the wire 156 is constructed of tungsten, the flow tube 154 can be constructed of a ceramic, such as Shapal-M.

At least one opening 180 is formed in the clamp member 158 to permit fluid to enter or exit the flow tube 154 through the opening 180. As shown in FIG. 9, the clamp member 158 can be provided with at least two openings 180 with each opening 180 having a semicircular shape. However, it should be understood that the shape of the openings 180 can vary depending on the desires of the designer. More specifically, it should be understood that the openings 180 can have any asymmetrical, symmetrical or fanciful shape.

The wire 156 is constructed in a similar manner to the wire 74 discussed above. The wire 156 is supported and tensioned within the flow tube 154 in a similar manner as the wire 74 is supported and tensioned within the housing 76. The signal paths 75a and 75b from the signal processor 66 and the analytical circuit 68 are connected to the respective connectors 152 in any suitable manner, such as screws, bolts, terminals or the like.

As discussed above, if $f_0$, the resonance in vacuum of equation (1), of the sensor unit 150 is stable, then it is possible to determine both density and viscosity from the measured complex voltages as a function of frequency over the resonance. Because the sensor unit 150 includes two metallic connectors 152 separated by the flow tube 154 formed from an electrically isolating material; these materials have different elastic and, in some cases, also thermal properties. The connectors 152 and the flow tube 154 are preferably held together solely by the tension of the wire 156.

The sensor unit 150 preferably has an $f_0$ unaffected by the fluid properties and pressure. The latter may have a small but yet calculable contribution from the wire material compressibility. In addition, the response of the wire 156 to temperature variations, that include differential thermal expansion arising from the use of dissimilar materials in the construction of the resonator, should either be measurable or calculable. The wire 156 is tensioned and set into transverse motion by passing an electrical current through it in the presence of a perpendicular magnetic field. These factors imply that the sensor unit 150 could be improved by eliminating rotational motion of the wire 156 that might arise from the wire 156 having an elliptical cross-section, and the sensor unit 150 must also electrically isolate each end of the wire 156 to permit current to flow through it.

Tungsten, despite the surface roughness, is the preferred material for the wire 156 for measurements involving liquid because both Youngs' modulus E($\approx$411 GPa) and density $\rho_s$($\approx$19,300 kg·m$^{-3}$) are high relative to other materials. When the wire 156 is tensioned the former assists in providing a stable resonance while the latter provides sensitivity to the fluid around it, through the ratio $\rho/\rho_s$ in equations (4) and (5). The effect of surface roughness is negligible provided the amplitude of vibration is small and Reynolds number less than 100. For measuring the density, it is desirable that the wire density tend toward the density of the fluid; derived from added mass concepts. Thus, Tungsten can be used but other materials of lower density are also acceptable depending upon the expected density of the fluid to be measured.

To minimize the effect of differential thermal expansion, this choice of wire material dictates the material to use for the connectors 152, flow tube 154 and tensioning mechanism. It is desirable that the mechanical properties of the electrically insulating material forming the flow tube 154 be as close as possible to those of the materials used for both the wire 156 and the connectors 152. For example, the effect of differential thermal expansion on the wire tension, as the temperature departs from ambient, could be reduced by choosing a material with linear thermal expansion coefficient equivalent to that of tungsten; Shapal-M, which is a high thermal conductivity machinable ceramic with a compressive strength of 1 GPa, has a linear thermal expansion coefficient $\alpha=(1/L)dL/dT=5.2\cdot 10^{-6}$ K$^{-1}$ at T=298 K while $\alpha$(W, 298 K)$\approx$4.5·10$^{-6}$ K$^{-1}$. Alternative materials for the insulating material might include either aluminum nitride or Macor, however, $\alpha$ for these materials is not equivalent to W.

Figure 11:
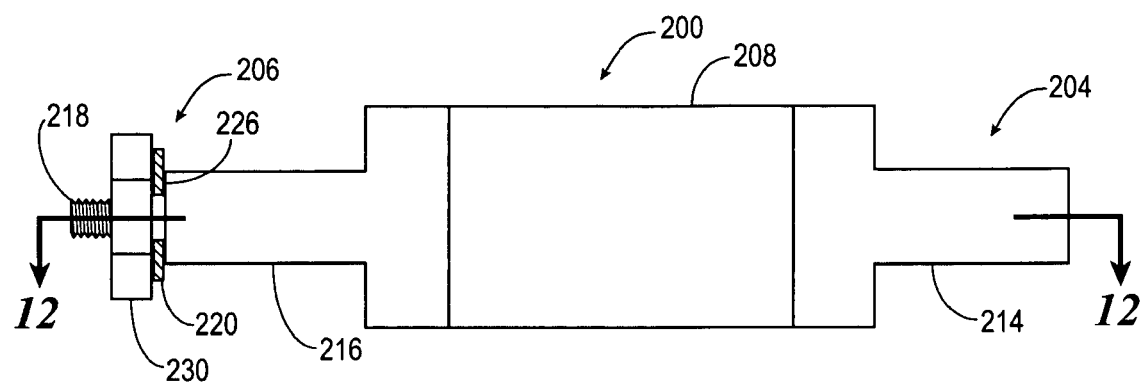
FIG. 11 is a side-elevational view of another version of a sensor unit.
Figure 12:
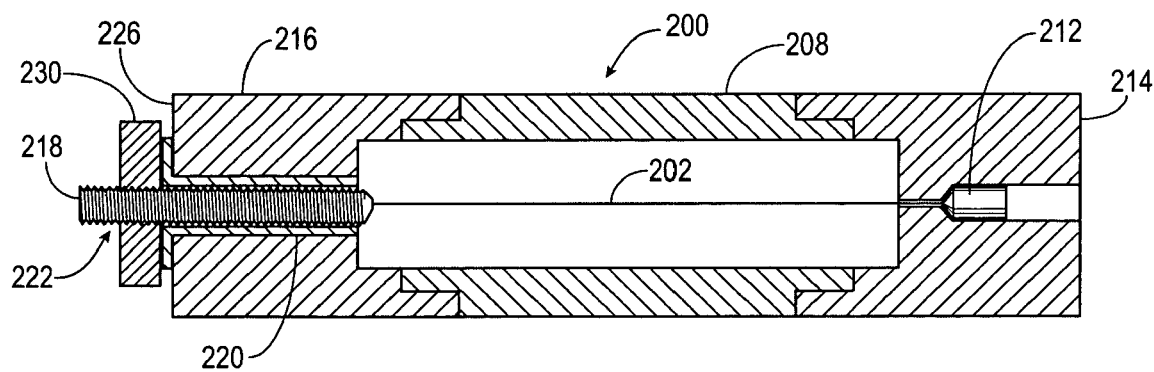
FIG. 12 is a cross-sectional view of the sensor unit of FIG. 11 taken along the lines 12—12 in FIG. 11.

The criteria described in the preceding paragraph were used to formulate another version of a sensor unit 200 for a vibrating wire viscometer-densimeter 60 shown in FIGS. 11 and 12 to reduce the variation in $f_0$ arising from temperature, pressure, and fluid properties. The sensor unit 200 is similar in construction and function as the sensor unit 150, with the exception that the temperature and pressure effects are reduced by constructing the sensor unit 200 mostly from a same material, such as tungsten, which has the same thermal expansion and elastic properties, while also minimizing the rotation of a wire 156 to reduce the effect on $f_0$ arising from variations in fluid properties. The sensor unit 200, shown in FIG. 11, consists of two connectors 204 and 206, both formed from tungsten and a flow tube 208 positioned between the connectors 204 and 206 within which the wire 202 is held. The wire 202 is rigidly connected to each connector 204 and 206. For example, in the example shown in FIGS. 11 and 12, the wire 202 is electron beam welded (EBW) to each connector 204 and 206.

The connector 204 includes a boss 212 and an end-piece 214. The boss 212 is connected to the wire 202 and is designed to prevent rotation of the wire 202. For example, the boss 212 can be provided with a non-circular cross-section, e.g., square, to prevent rotation of the wire 202. The boss 212 is positioned within a cavity formed in the end-piece 214. The boss 212 is shaped to facilitate alignment with the connector 206. The boss 212 can be formed from any shape suitable for facilitating alignment with the connector 206. For example, the boss 212 can include a tapered or conical end to facilitate alignment with the connector 206. The wire 202 can be attached to the boss 212 via any suitable manner that rigidly fixes the wire 202 to the boss 212. For example, the wire 202 can be positioned within a slot (not shown) formed in the boss 212 and electron beam welded as described above such that the boss 212 forms a clamp about the wire 202.

The connector 206 is provided with an end-mount 216, a boss 218, an insulator 220 and an adjustment assembly 222 for adjusting the relative positions of the boss 218 and the end-mount 216. The boss 218 is connected to the wire 202 in the same manner as the boss 212 is connected to the wire 202. The boss 218 is designed to prevent rotation of the wire. For example, the boss 218 can be provided with a non-circular cross-section, e.g., square, to prevent rotation of the wire 202. The boss 218 is positioned within a cavity 224 formed in the end-piece 216.

The insulator 220 provides electrical isolation between the end-piece 216 and the boss 218. In the embodiment shown in FIGS. 11 and 12, the insulator 220 is formed as a sleeve lining the cavity 224 within the end-piece 216 and extending across a face 226 of the end-piece 216. The insulator 220 can be formed of any insulating material capable of withstanding a down hole environment. For example, the insulator 220 can be constructed of a ceramic material, such as Shapal-M.

The adjustment assembly 222 can be any device capable of adjusting the relative positions between the boss 212 and the end-piece 216 to permit adjustment of the tension in the wire 202. For example, the adjustment assembly 222 can include a wire tensioning nut 230 that is threaded to the boss 212. Of course, there are many other arrangements that could be used to clamp the wire 202 to a housing to permit tensioning of the wire 202. For example, between two clamps or connectors as shown, or the use of a spring.

Figure 13:
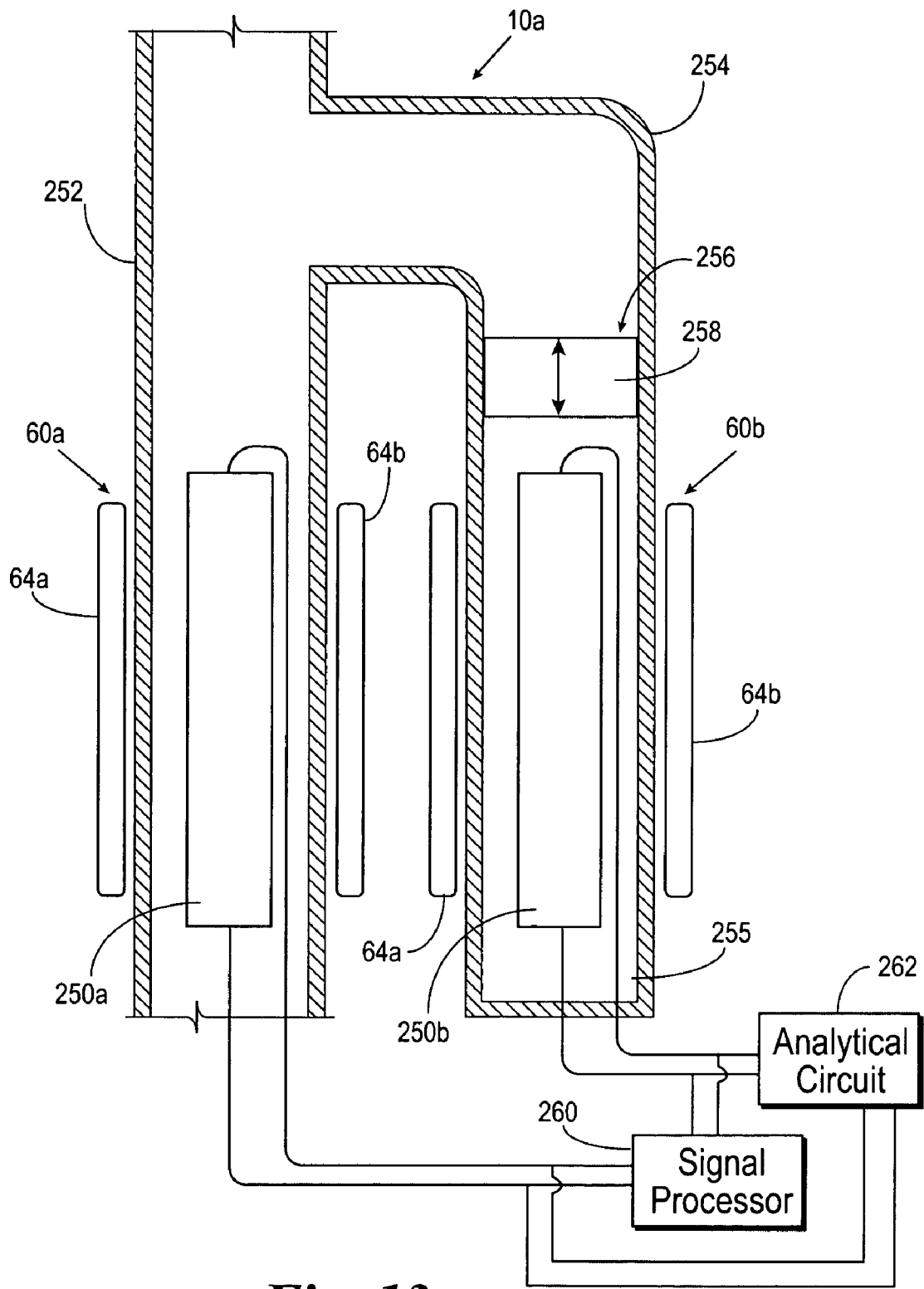
FIG. 13 is a fragmental, schematic representation of another version of a down hole tool having two or more viscometer-densimeters with one of the viscometer-densimeters positioned within a fluid of unknown viscosity and density and another one of the viscometer-densimeters positioned within a fluid of known viscosity and density.

As discussed above, it is desirable for the tensioned vibrating wire 74, 156 or 202 to have a stable resonance frequency with respect to temperature, pressure and fluid. A stable resonance frequency essentially reduces to a requirement of constant wire tension. Although it is plausible to construct a stable oscillator solely from mechanical considerations, another solution is afforded by the concept of relative measurements. Shown in FIG. 13 is a fragmental view of another version of a down hole 10*a* which is similar in construction and function to the down hole 10, discussed above, except that the down hole tool 10*a* has two or more viscometer-densimeters 60 with one of the viscometer-densimeters 60 (designated as 60*a*) positioned within a fluid of unknown viscosity and density and another one of the viscometer-densimeters 60 (designated as 60*b*) positioned within a fluid of known viscosity and density. Each of the viscometer-densimeters 60*a* and 60*b* are provided with magnets 64*a*, 64*b*. In this approach, two similar sensor units 250*a* and 250*b* are used with one immersed in the fluid of unknown properties, e.g., density and viscosity, and the other in the fluid of known properties. The sensor units 250*a* and 250*b* can be constructed in a manner described above with respect to the sensor units 62, 150 or 200 described above.

The sensor unit 250*a* is positioned within an evaluation flow line 252, which can be the evaluation flow line 46, the cleanup flow line 46*a* or the sample chamber 50 discussed above. In the down hole tool 10*a*, an elbow or joint 254 is provided that is in fluid communication with the flow line 252. The joint 254 defines a comparison chamber 255 in which the known fluid and the sensor unit 250*b* are positioned. The down hole tool 10*a* is provided with a pressure equalization assembly 256 for equalizing the pressure within the evaluation flow line 252. In general, the pressure equalization assembly 256 can be any device capable of equalizing the pressure between the evaluation flow line 252 and the comparison chamber 255. For example, as shown in FIG. 13, the pressure equalization assembly 256 can include a reciprocating piston 258 which moves relative to the comparison chamber 255 to equalize the pressure.

The sensor units 250*a* and 250*b* are connected to one or more signal processor 260 and analytical circuit 262 for providing the drive voltage and determining one or more fluid parameters, such as viscosity and density, as discussed above. The signal processor 260 and the analytical circuit 262 are similar in construction and function to the signal processor 66 and the analytical circuit 68 discussed above.

Figure 14A:
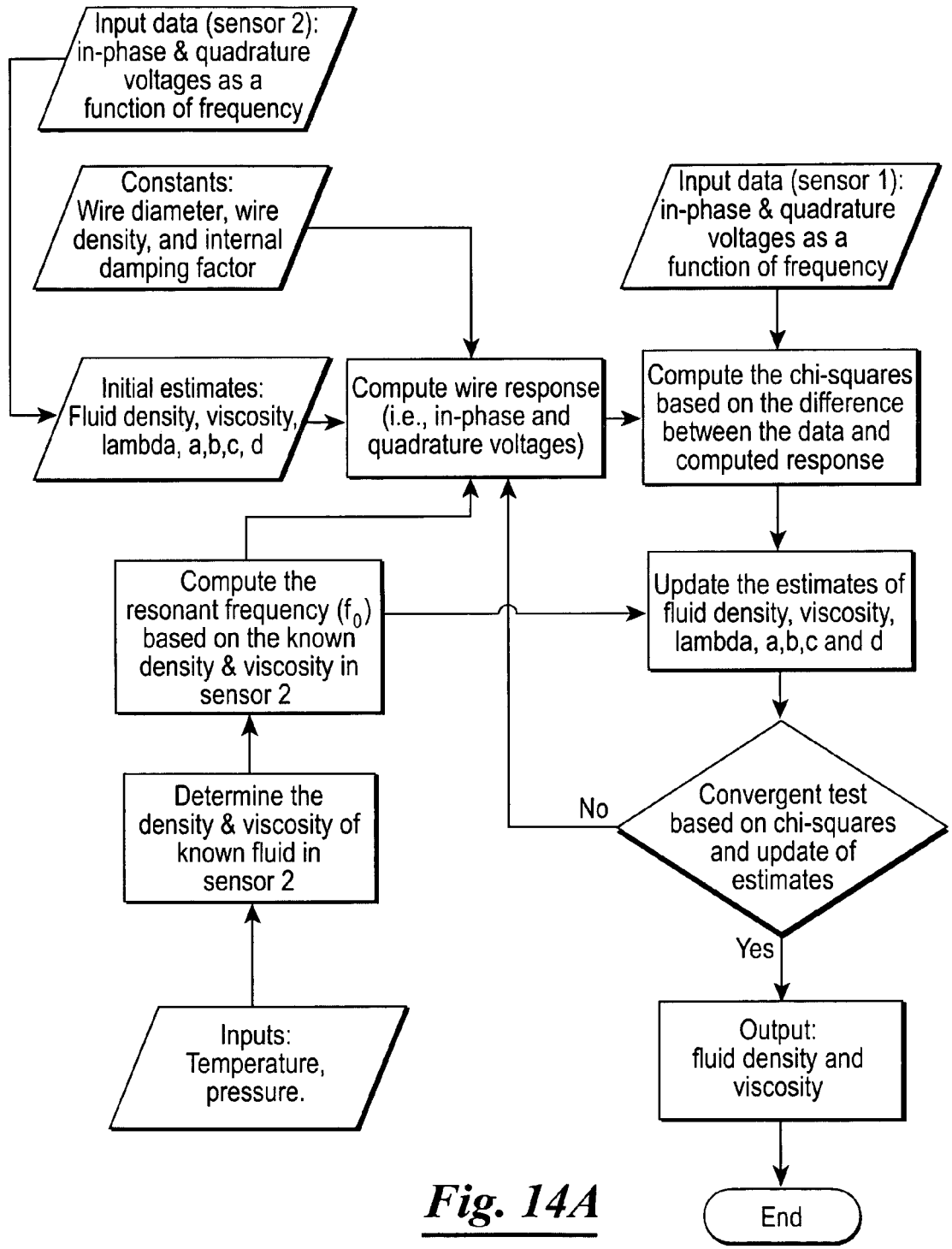
FIG. 14a is a logic flow diagram illustrating a method for simultaneously calculating viscosity and density utilizing the arrangement shown in FIG. 13.
Figure 14B:
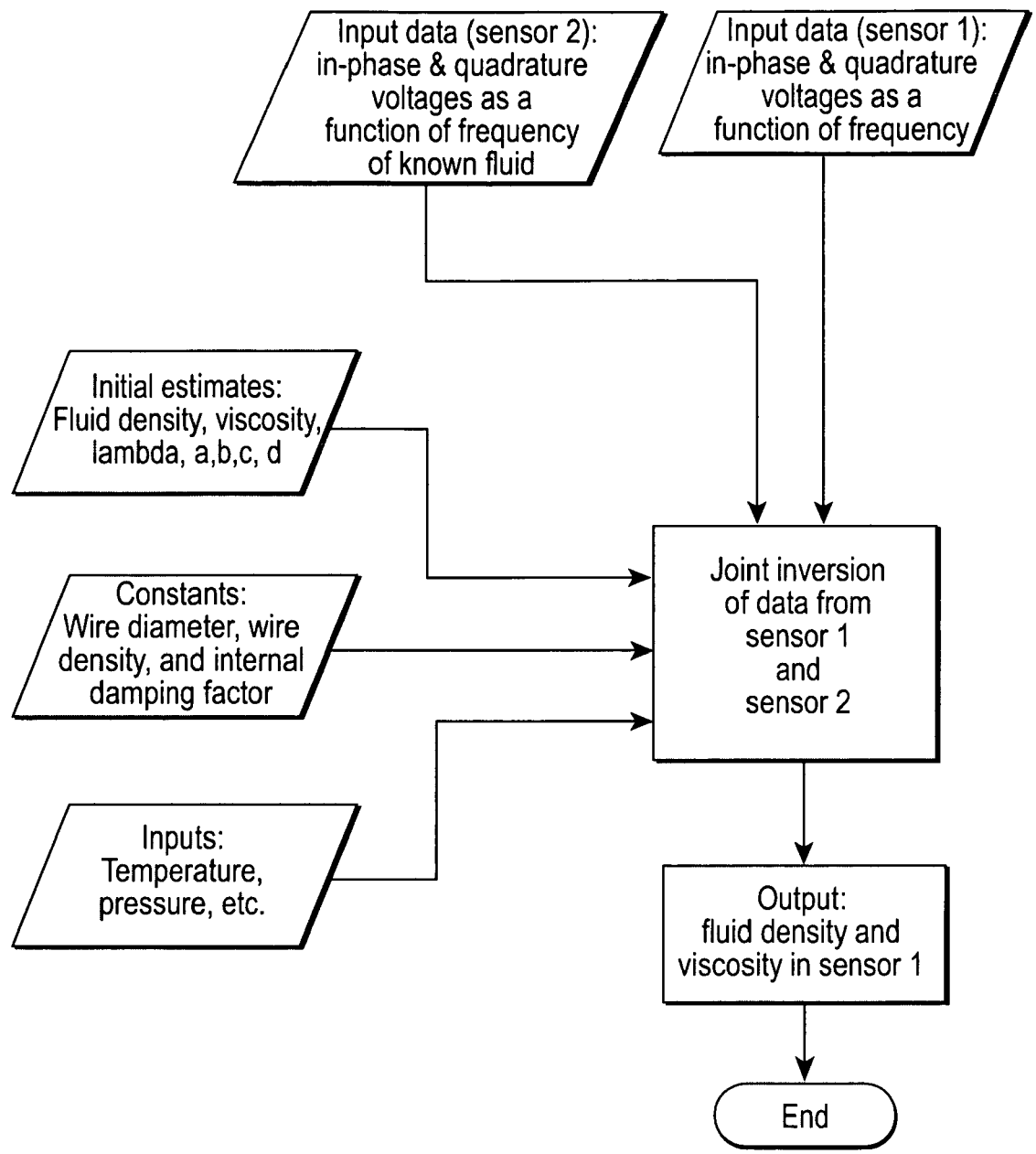
FIG. 14b is a logic flow diagram illustrating another method for simultaneously calculating viscosity and density utilizing the arrangement shown in FIG. 13.

The ratio of the resonances between the sensor units 250*a* and 250*b* are determined as illustrated, for example, in FIGS. 14*a* and 14*b*. FIG. 14*a* shows a process 170 for calculating the density and viscosity of the fluid utilizing the dual viscometer-densimeters 60*a* and 60*b* illustrated in FIG. 13. The process 170 has similar steps to those utilized in FIG. 7*a* discussed above. For purposes of clarity, the similar steps are labeled with the same reference numerals 134*a*, 134*b*, 134*d*, 134*e*, 134*f*, 134*g*, 134*h* and 134*i* and will not be described in detail again.

In general, the density and the viscosity of the fluid which will be in the comparison chamber 255 is determined by known methods, such as using tables from the United States National Institute of Standards and Technology (NIST) as indicated by steps 172 and 174. The analytical circuit 262 receives signals from the sensor unit 250*b* as indicated by a step 176, and then calculates the resonant frequency based on the known density and viscosity of the fluid within the comparison chamber 255 as indicated by a step 178. The analytical circuit 262 then computes the viscosity and density in the manner described above with respect to FIG. 7A.

Shown in FIG. 14B is another process 180 for computing the fluid density and viscosity of the unknown fluid within the flow line 252. In the process 180, initial estimates of the fluid density, viscosity and lambda a, b, c, and d are input into the analytical circuit 262 as indicated by blocks 182 and 183. Constants, such as wire diameter, wire density and internal damping factor are input into the analytical circuit 262 as indicated by a block 184. Other inputs, such as the temperature and pressure that the sensor unit 250*a* in the flow line 252 is being exposed to are input into the analytical circuit 262 as indicated by a block 186. The input data, such as in-phase and quadrature data, are then read from the sensor units 250*a* and 250*b* as represented by blocks 188 and 190 and a joint inversion of the data from sensor 250*a* and 250*b* is computed as indicated by the block 183. The analytical circuit 262 then outputs the fluid density and the viscosity of the fluid surrounding the sensor unit 250*a* as indicated by a block 192.

Although the two foregoing methods for calculating viscosity and density have been described above, it should be understood that any manner could be utilized, such as a ratio measurement of the outputs generated by the two sensor units 250*a* and 250*b*.

Provided the wires within the sensor units 250*a* and 250*b* are of similar construction (preferably identical construction) and exposed to the same temperature and pressure any instabilities arising from these variables is eliminated and data is obtained indicative of a stable oscillator. If both concepts are combined, that is a comparison or ratio measurement and a stable geometry as recited above with respect to the sensor units 150 and 200, then it is plausible that the resonator will be stable and be able to provide both density and viscosity. It will be understood from the foregoing description that various modifications and changes may be made in the preferred and alternative embodiments of the present invention without departing from its true spirit. The devices included herein may be manually and/or automatically activated to perform the desired operation. The activation may be performed as desired and/or based on data generated, conditions detected and/or analysis of results from down hole operations.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A down hole tool positionable in a well bore penetrating a subterranean formation, the down hole tool adapted to convey at least a portion of a fluid in the formation to a viscometer-densimeter via a flowline disposed between the viscometer-densimeter and the formation, the viscometer-densimeter comprising:
- a sensor unit positionable within the down hole tool, the sensor unit comprising:
  - at least two spatially disposed connectors;
  - a wire suspended in tension between the at least two connectors such that the wire is available for interaction with the fluid when the viscometer-densimeter is positioned within the down hole tool and the down hole tool is positioned within the subterranean formation and receives the fluid from the subterranean formation, the connectors and the wire constructed so as to provide a frequency oscillator; and
  - at least one magnet emitting a magnetic field interacting with the wire.

2. A down hole tool positionable in a well bore having a wall and penetrating a subterranean formation, the formation having a fluid therein, the down hole tool comprising:
- a housing enclosing at least one evaluation cavity;
- a fluid communication device extendable from the housing for sealing engagement with the wall of the well bore, the fluid communication device having at least one inlet communicating with the evaluation cavity for receiving the fluid from the formation and depositing such fluid into the evaluation cavity; and
- a viscometer-densimeter comprising:
  - a sensor unit positioned within the evaluation cavity, the sensor unit comprising:
    - at least two spatially disposed connectors; and
    - a wire suspended in tension between the at least two connectors such that the wire is available for interaction with the fluid within the evaluation cavity, the connectors and the wire constructed so as to provide a frequency oscillator; and
    - at least one magnet emitting a magnetic field interacting with the wire.

3. The down hole tool of claim 2, wherein the connectors and the wire are constructed of a single type of material.

4. The down hole tool of claim 2, further comprising means for preventing rotation of the wire with respect to the connectors.

5. The down hole tool of claim 4, wherein the means for preventing rotation of the wire further comprises a boss connected to the wire, the boss having a non-circular cross-section.

6. The down hole tool of claim 2, further comprising an analytical circuit receiving feedback from the wire for calculating at least two parameters of fluid interacting with the wire.

7. The down hole tool of claim 6, wherein the two parameters are viscosity and density.

8. The down hole tool of claim 1, wherein the connectors and the wire are constructed of materials having similar coefficients of thermal expansion so as to provide the frequency oscillator.

9. The down hole tool of claim 1, further comprising a flow tube in which the wire is suspended by the connectors; and wherein the flow tube, the connectors and the wire are constructed of materials having similar coefficients of thermal expansion so as to provide the frequency oscillator.

10. The down hole tool of claim 1, further comprising a comparison chamber containing a fluid of known properties with the down hole conditions within the comparison chamber being similar to the down hole conditions within the evaluation cavity; and wherein the down hole tool is also provided with a second sensor within the comparison chamber such that the down hole includes the one sensor unit positioned within a fluid of unknown parameters within the evaluation cavity and the second sensor positioned with a fluid of known parameters within the comparison chamber.

* * * * *